US007883478B2

(12) United States Patent
Skinner et al.

(10) Patent No.: US 7,883,478 B2
(45) Date of Patent: Feb. 8, 2011

(54) PATIENT SUPPORT HAVING REAL TIME PRESSURE CONTROL

(75) Inventors: Andrew F. Skinner, Batesville, IN (US); Colin Clarke, Victoria (CA); Michael Z. Sleva, Wyoming, OH (US); Richard B. Stacy, Daniel Island, SC (US); Robert Petrosenko, Daniel Island, SC (US); John A. Bobey, Daniel Island, SC (US); Jonathan H. Mueller, Mt. Pleasant, SC (US); Sohrab Soltani, Charleston, SC (US); David Lokhorst, Victoria (CA); Mayur Yermaneni, Cincinnati, OH (US); Daniel Stevens, Summerville, SC (US); Gregory W. Branson, Batesville, IN (US)

(73) Assignee: Hill-Rom Services, Inc., Wilmington, DE (US)

(*) Notice: Subject to any disclaimer, the term of this patent is extended or adjusted under 35 U.S.C. 154(b) by 1311 days.

(21) Appl. No.: 11/119,991

(22) Filed: May 2, 2005

(65) Prior Publication Data

US 2006/0075559 A1 Apr. 13, 2006

Related U.S. Application Data

(60) Provisional application No. 60/665,241, filed on Mar. 25, 2005, provisional application No. 60/665,141, filed on Mar. 25, 2005, provisional application No. 60/636,252, filed on Dec. 15, 2004, provisional application No. 60/608,013, filed on Sep. 8, 2004, provisional application No. 60/567,215, filed on Apr. 30, 2004.

(51) Int. Cl.

*A61B 5/103* (2006.01)
*A61B 5/117* (2006.01)
*A47C 16/00* (2006.01)
*A47C 27/08* (2006.01)
*A47C 27/10* (2006.01)

(52) U.S. Cl. ........................ 600/595; 600/587; 5/655.3; 5/706; 5/710; 5/713

(58) Field of Classification Search ................ 600/595; 5/655.3, 706, 710, 713

See application file for complete search history.

(56) References Cited

U.S. PATENT DOCUMENTS 3,492,988 A 2/1970 De Mare (Continued)

FOREIGN PATENT DOCUMENTS

CA 2 393 880 A1 1/2004

(Continued)

OTHER PUBLICATIONS

Hill-Rom PrimeAire ARS Pressure Relief Mattress, Date Unknown.

(Continued)

*Primary Examiner*—Max Hindenburg
*Assistant Examiner*—Adam J. Eiseman
(74) *Attorney, Agent, or Firm*—Barnes & Thornburg LLP

(57) ABSTRACT

A patient support having real time pressure control. The patient support includes a plurality of sensors located beneath a bladder including a plurality of upright cylindrical elements. The pressure within the bladder is controlled based on the pressure or force sensed by the plurality of sensors.

20 Claims, 14 Drawing Sheets

U.S. PATENT DOCUMENTS

| | | | | |
|---|---|---|---|---|
| 4,839,512 | A | 6/1989 | Speck | |
| 4,907,308 | A | 3/1990 | Leininger et al. | |
| 5,060,174 | A | 10/1991 | Gross | |
| 5,117,518 | A | 6/1992 | Schild | |
| 5,163,196 | A | 11/1992 | Graebe et al. | |
| 5,170,364 | A * | 12/1992 | Gross et al. | 702/139 |
| 5,269,030 | A | 12/1993 | Pahno et al. | |
| 5,316,041 | A | 5/1994 | Ramacier, Jr. et al. | |
| 5,364,162 | A | 11/1994 | Bar et al. | |
| 5,561,875 | A | 10/1996 | Graebe | |
| 5,596,781 | A | 1/1997 | Graebe | |
| 5,630,238 | A | 5/1997 | Weismiller et al. | |
| D386,035 | S | 11/1997 | Matsler et al. | |
| 5,689,845 | A | 11/1997 | Sobieralski | |
| 5,715,548 | A | 2/1998 | Weismiller et al. | |
| 5,815,864 | A | 10/1998 | Sloop | |
| 5,829,081 | A | 11/1998 | Pearce | |
| 5,845,352 | A | 12/1998 | Matsler et al. | |
| 5,873,137 | A | 2/1999 | Yavets-Chen | |
| D407,353 | S | 3/1999 | Bar et al. | |
| D408,767 | S | 4/1999 | Bar et al. | |
| 5,917,180 | A | 6/1999 | Reimer et al. | |
| D412,685 | S | 8/1999 | Bar et al. | |
| D413,085 | S | 8/1999 | Bar et al. | |
| D413,841 | S | 9/1999 | Bar et al. | |
| 5,954,402 | A | 9/1999 | McInturff | |
| D415,567 | S | 10/1999 | Bar | |
| D415,834 | S | 10/1999 | Bar | |
| 5,970,789 | A | 10/1999 | Meyer et al. | |
| D416,326 | S | 11/1999 | Bar | |
| 5,984,418 | A | 11/1999 | McInturff | |
| 6,014,346 | A | 1/2000 | Malone | |
| 6,058,537 | A * | 5/2000 | Larson | 5/710 |
| 6,076,208 | A | 6/2000 | Heimbrock et al. | |
| 6,095,611 | A | 8/2000 | Bar et al. | |
| 6,145,142 | A | 11/2000 | Rechin et al. | |
| 6,165,142 | A | 12/2000 | Bar | |
| D439,098 | S | 3/2001 | Matsler et al. | |
| 6,212,718 | B1 | 4/2001 | Stolpmann et al. | |
| 6,240,584 | B1 | 6/2001 | Perez et al. | |
| 6,320,510 | B2 | 11/2001 | Menkedick et al. | |
| 6,378,152 | B1 | 4/2002 | Washburn et al. | |
| D463,701 | S | 10/2002 | Borcherding et al. | |
| 6,474,743 | B1 | 11/2002 | Harker et al. | |
| 6,487,739 | B1 | 12/2002 | Harker | |
| 6,499,167 | B1 | 12/2002 | Ellis et al. | |
| 6,560,804 | B2 | 5/2003 | Wise et al. | |
| 6,564,410 | B2 | 5/2003 | Graebe et al. | |
| 6,593,588 | B1 | 7/2003 | Reimer | |
| 6,623,080 | B2 | 9/2003 | Clapper | |
| 6,646,556 | B1 | 11/2003 | Smith et al. | |
| 6,687,936 | B2 | 2/2004 | Graebe et al. | |
| 6,687,937 | B2 | 2/2004 | Harker | |
| 6,701,556 | B2 | 3/2004 | Romano et al. | |
| 6,721,980 | B1 * | 4/2004 | Price et al. | 5/713 |
| 6,735,799 | B1 | 5/2004 | Ellis et al. | |
| 6,760,939 | B2 | 7/2004 | Ellis et al. | |
| 6,848,135 | B1 | 2/2005 | Kohlman | |
| 6,877,178 | B2 | 4/2005 | Chapman et al. | |
| 2001/0011480 | A1 | 8/2001 | Reimer | |
| 2002/0066143 | A1 | 6/2002 | Graebe et al. | |
| 2003/0030319 | A1 | 2/2003 | Clapper | |
| 2006/0010607 | A1 * | 1/2006 | Schneider | 5/713 |

FOREIGN PATENT DOCUMENTS

| | | | |
|---|---|---|---|
| DE | 103 16 162 | A1 | 10/2004 |
| DE | 103 33 742 | A1 | 10/2005 |
| EP | 853 918 | A2 | 7/1998 |
| FR | 2814062 | | 3/2002 |
| WO | WO 2004/006768 | A1 | 1/2004 |
| WO | WO 2005/013878 | | 2/2005 |

OTHER PUBLICATIONS

A Hill-Rom solution, ACUCAIRE Continuous Airflow System, Date Unknown.

The International Search Report and The Written Opinion for PCT/US06/26787, dated Mar. 6, 2008, (8 pages).

* cited by examiner

PATIENT SUPPORT HAVING REAL TIME PRESSURE CONTROL

CROSS-REFERENCE TO RELATED APPLICATIONS

This application claims the benefit of U.S. Provisional Patent Application Ser. No. 60/567,215 to Balaton et al., entitled PRESSURE RELIEF SUPPORT SURFACE, filed Apr. 30, 2004, and U.S. Provisional Patent Application Ser. No. 60/665,241 of Hopkins et al., entitled THERMOREGULATING DEVICE WITH SUPPORT CELLS, filed Mar. 25, 2005, and U.S. Provisional Patent Application Ser. No. 60/665,141 of Hopkins et al., entitled THERMOREGULATING DEVICE, filed Mar. 25, 2005, and U.S. Provisional Patent Application Ser. No. 60/636,252 of Chambers et al., entitled QUICK CONNECTOR FOR MULTIMEDIA, filed Dec. 15, 2004, and U. S. Provisional Patent Application Ser. No. 60/608,013 of Branson, entitled ROTATION SENSOR FOR A MATTRESS, filed Sep. 8, 2004, all of which are assigned to the assignee of the present invention, and all of which are incorporated herein by this reference in their entirety.

The present application is also related to U.S. patent application Ser. No. 11/120,080, entitled PATIENT SUPPORT, U.S. patent application Ser. No. 11/119,980, entitled PRESSURE RELIEF SURFACE, and U.S. patent application Ser. No. 11/119,635, entitled LACK OF PATIENT MOVEMENT MONITOR AND METHOD, all of which are filed on the same date herewith, are assigned to the assignee of the present invention, and are incorporated herein by this reference.

In addition, PCT patent application, entitled BODY SUPPORT APPARATUS HAVING AUTOMATIC PRESSURE CONTROL AND RELATED METHODS of Lokhorst et al. PCT/CA05/00658 filed on the same date herewith is incorporated herein in its entirety.

BACKGROUND

The present invention relates to a device for supporting a patient, such as a mattress. In particular, the present invention relates to patient supports appropriate for use in hospitals, acute care facilities, and other patient care environments. Further, the present invention relates to pressure relief support surfaces and support surfaces that are configured to accommodate and operate with a variety of sizes and styles of beds, bed frames, and patient types.

Known patient supports are disclosed in, for example, U.S. Pat. No. 5,630,238 to Weismiller et al., U.S. Pat. No. 5,715,548 to Weismiller et al., U.S. Pat. No. 6,076,208 to Heimbrock et al., U.S. Pat. No. 6,240,584 to Perez et al., U.S. Pat. No. 6,320,510 to Menkedick et al., U.S Pat. No. 6,378,152 to Washburn et al., and U.S. Pat. No. 6,499,167 to Ellis et al., all of which are owned by the assignee of the present invention and all of which are incorporated herein by this reference.

SUMMARY

The present invention provides an apparatus and method for minimizing the interface pressure between a support surface and a person or patient on the surface.

In the illustrated embodiment of the present invention, a pressure adjustable mattress system. The mattress system includes a plurality of air bladders, a plurality of force sensors, each of the plurality of pressure sensors subtending at least one of the plurality of air bladders to sense a force transmitted through the subtended air bladder, and a plurality of outputs, to transmit a signal representative of a sensed force, each of the plurality of outputs coupled to at least one of the plurality of force sensors.

According to another aspect of the present invention there is provided a method for adjusting the pressure of a pressure adjustable mattress to a pressure value, the mattress including a plurality of force sensors wherein each of the plurality of force sensors generates a force signal representative of a sensed force transmitted through the pressure adjustable mattress. The method includes the steps of ordering the force signals in a predetermined order, calculating an indicator signal as a function of the ordered force signals, comparing the indicator signal to the predetermined value to generate a correction signal, and adjusting the pressure of the pressure adjustable mattress based on the correction signal.

Also there is provided in a pressure adjustable support, including a bladder to support a patient and having a pressure therein, a sensor subtending the bladder to sense a force transmitted through the bladder and generating a signal responsive to the sensed force a method. The method includes the steps of detecting a position of the patient on the bladder with the sensor, detecting movement of the patient on the bladder with the sensor, and adjusting the pressure within the bladder responsive to the detected position and the detected movement of the patient.

With respect to another aspect of the present invention, there is provided in a pressure adjustable support, including a bladder assembly having a plurality of vertical bladders, to support a patient, a plurality of sensors, each of the plurality of sensors subtending at least one of the vertical bladders to sense a force transmitted through the vertical bladders, a method. The method includes the steps of detecting a position of the patient on the plurality of vertical bladders with the plurality of sensors, detecting movement of the patient on the plurality of vertical bladders with the plurality of sensors, and adjusting the pressure within the bladder responsive to the detected position and the detected movement of the patient.

BRIEF DESCRIPTION OF THE DRAWINGS

Aspects of the present invention are more particularly described below with reference to the following figures, which illustrate an exemplary embodiment of the present invention.

DETAILED DESCRIPTION

Figure 1:
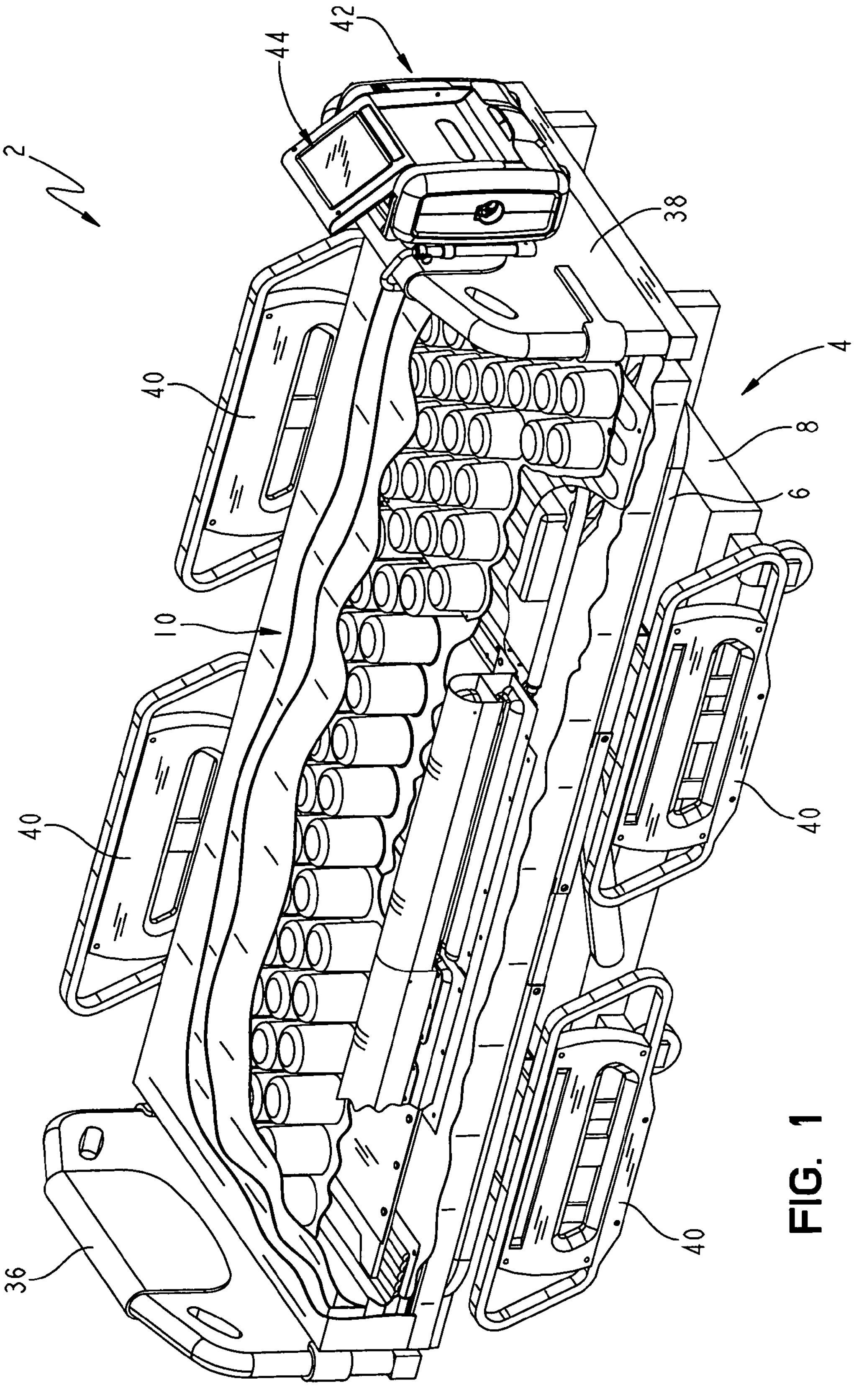
FIG. 1 is a perspective view of a patient support positioned on an exemplary hospital bed, with a portion of the patient support being cut away to show interior components of the patient support.

FIG. 1 shows an embodiment of a patient support 10 in accordance with the present invention. Patient support 10 is positioned on an exemplary bed 2. Bed 2, as illustrated, is a hospital bed including a frame 4, a headboard 36, a footboard 38, and a plurality of siderails 40.

Frame 4 of the exemplary bed 2 generally includes a deck 6 supported by a base 8. Deck 6 includes one or more deck sections (not shown), some or all of which may be articulating sections, i.e., pivotable with respect to base 8. In general, patient support 10 is configured to be supported by deck 6.

Patient support 10 has an associated control unit 42, which controls inflation and deflation of certain internal components of patient support 10. Control unit 42 includes a user interface 44, which enables caregivers and service providers to configure patient support 10 according to the needs of a particular patient. For example, support characteristics of patient support 10 may be adjusted according to the size, weight, position, or activity of the patient.

User interface 44 also enables patient support 10 to be adapted to different bed configurations. For example, deck 6 may be a flat deck or a step deck. A caregiver may select the appropriate deck configuration via user interface 44. An exemplary control unit 42 and user interface 44 are described in detail in U.S. Provisional Patent Application Ser. No. 11/119,635, filed on the same date herewith, assigned to the assignee of the present invention, and incorporated herein by reference.

Figure 2:
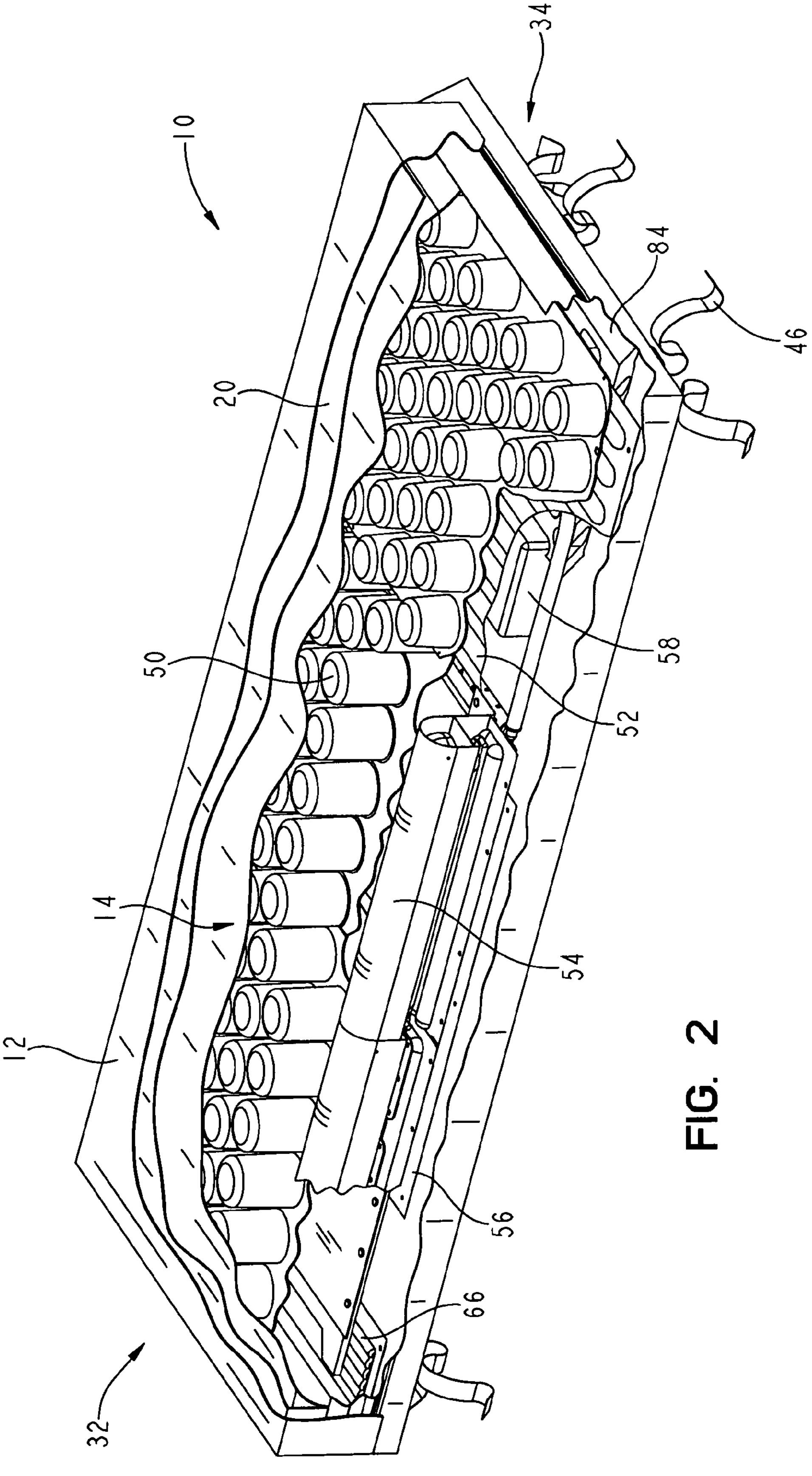
FIG. 2 is a perspective view of a patient support, with a portion being cut away to show interior components of the patient support.

Referring now to FIG. 2, patient support 10 has a head end 32 configured to support a patient's head and upper body region, and a foot end 34 configured to support a patient's feet and lower body region. Patient support 10 includes a cover 12 which defines an interior region 14. In the illustrated embodiment, interior region 14 includes a first layer 20, a second layer 50, and a third layer 52.

As shown in FIG. 2, first layer 20 includes a three-dimensional material, second layer 50 includes a plurality of vertically-oriented air bladders located underneath the first layer, and third layer 52 includes a plurality of pressure sensors located underneath the vertical bladders of second layer 50, as more particularly described below.

Also located within interior region 14 are a plurality of bolsters 54, a plurality of filler portions 56, and a pneumatic valve control box 58. A fire-resistant material (not shown) may also be included in the interior region 14.

Patient support 10 may be coupled to deck 6 by one or more couplers 46. Illustratively, couplers are conventional woven straps including a Velcro® brand or similar fastener. However, it is understood that other suitable couplers may be used.

Figure 3:
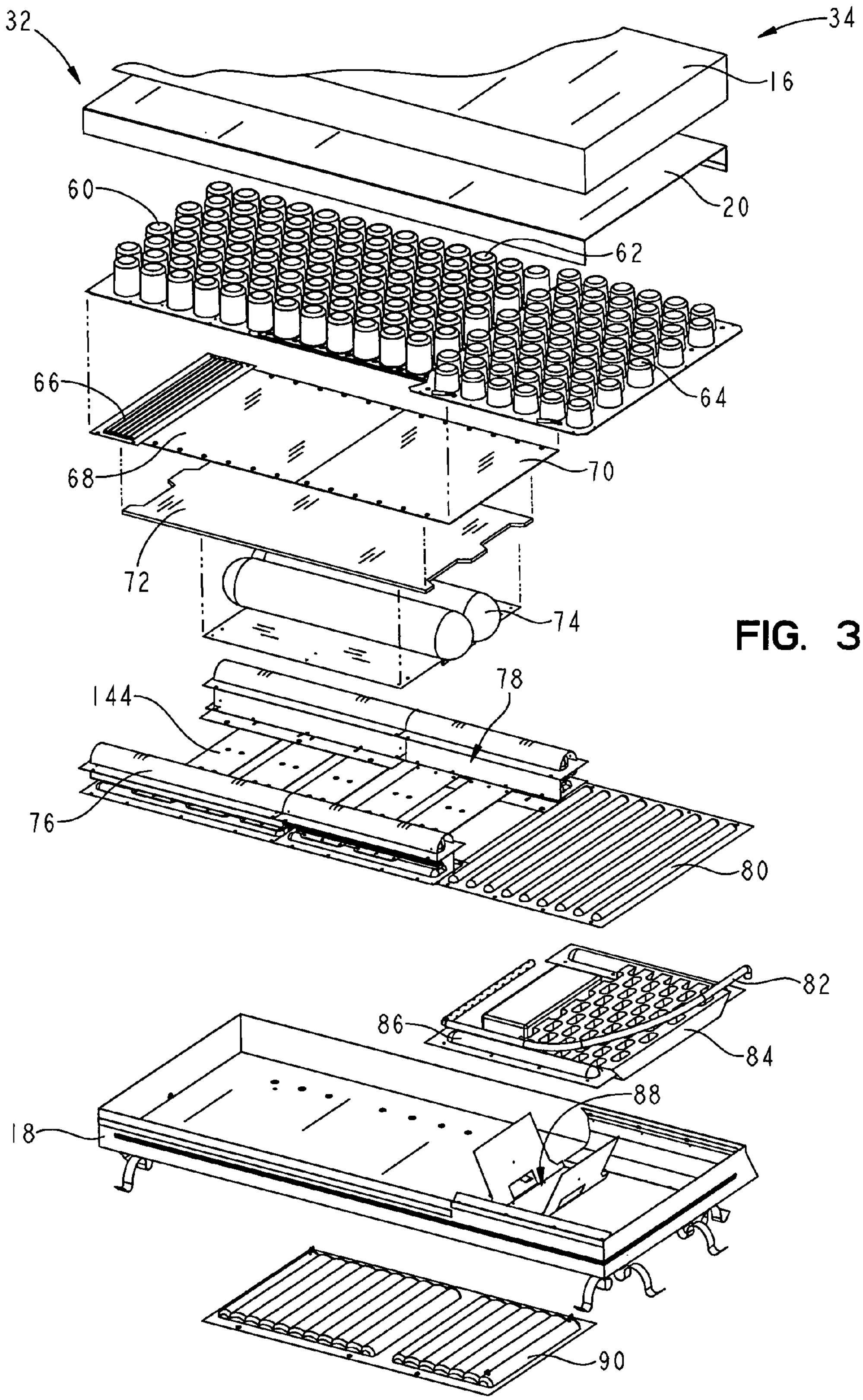
FIG. 3 is an exploded view of components of a patient support.

Components of one embodiment of a patient support in accordance with the present invention are shown in exploded view in FIG. 3. This embodiment of patient support 10 includes a top cover portion 16 and a bottom cover portion 18. Top cover portion 16 and bottom cover portion 18 couple together by conventional means (such as zipper, Velcro®, snaps, buttons, or other suitable faster) to form cover 12, which defines interior region 14. While a plurality of layers and/or components are illustrated within interior region 14, it will be understood by those of skill in the art that the present invention does not necessarily require all of the illustrated components.

A first support layer 20 is located below top cover portion 16 in interior region 14. Support layer includes one or more materials, structures, or fabrics suitable for supporting a patient, such as foam, inflatable bladders, or three-dimensional material. Suitable three-dimensional materials include Spacenet® and/or Tytex™-brand or similar materials.

A second support layer including one or more bladder assemblies, is located underneath the first support layer 20. The illustrated embodiment of the second support layer includes first, second and third bladder assemblies, namely, a head section bladder assembly 60, a seat section bladder assembly 62, and a foot section bladder assembly 64. However, it will be understood by those skilled in the art that other embodiments include only one bladder assembly extending from head end 32 to foot end 34, or other arrangements of multiple bladder assemblies, for example, including an additional thigh section bladder assembly.

A pressure-sensing layer illustratively including first and second sensor pads, namely a head sensor pad 68 and a seat sensor pad 70, is positioned underneath bladder assemblies 60, 62, 64. Head sensor pad 68 is generally aligned underneath head section bladder assembly 60, and seat sensor pad 70 is generally aligned underneath seat section bladder assembly 62, as shown. It will be understood by those skilled in the art that other embodiments include a single sensor pad or additional sensor pads, for example, located underneath foot section bladder assembly 64, and/or different alignments of the sensor pads.

In the illustrated embodiment, a turn-assist cushion 74 is located below sensor pads 68, 70. The exemplary turn-assist cushion 74 shown in FIG. 3 includes a pair of inflatable bladders. Suitable turn-assist cushions are disclosed in, for example, U.S. Pat. No. 6,499,167 to Ellis, et al., which patent is owned by the assignee of the present invention and incorporated herein by this reference. One of ordinary skill in the art will readily appreciate that turn-assist cushions 74 are not necessarily a required element of the present invention.

A plurality of other support components 66, 72, 76, 78, 80, 84, 86, 90 are also provided in the illustrated embodiment of FIG. 3. One or more of these support components are provided to enable patient support 10 to be used in connection with a variety of different bed frames, in particular, a variety of bed frames having different deck configurations. One or more of these support components may be selectively added to or removed from patient support 10 in order to conform patient support 10 to a particular deck configuration, such as a step or recessed deck or a flat deck.

The support components illustrated in FIG. 3 are made of foam, inflatable bladders, three-dimensional material, other suitable support material, or a combination of these. For example, as illustrated, head filler 66 includes a plurality of foam ribs extending transversely across patient support 10. Filler portion 72 includes a foam layer positioned substantially underneath the sensor pads 68, 70 and extending transversely across the patient support 10.

Head bolster assembly 76 and seat bolster assembly 78 each include longitudinally-oriented inflatable bladders spaced apart by coupler plates 144.

As illustrated, first foot filler portion 80 includes a plurality of inflatable bladders extending transversely across patient support 10, and second foot filler portion 84 includes a foam member, illustratively with portions cut out to allow for retractability or for other reasons. Deck filler portion 90 includes a plurality of transversely-extending inflatable bladders. As illustrated, deck filler portion 90 includes two bladder sections, and is located outside of cover 12. However, one of ordinary skill in the art will recognize that deck filler portion 90 may include one or more bladder regions, or may be located within interior region 14, without departing from the scope of the present invention.

Also provided in the illustrated embodiment are a pneumatic valve box 58 and an air supply tube assembly 82. Receptacle 88 is sized to house pneumatic valve box 58. In the illustrated embodiment, receptacle 88 is coupled to bottom cover portion 18.

Figure 4A:
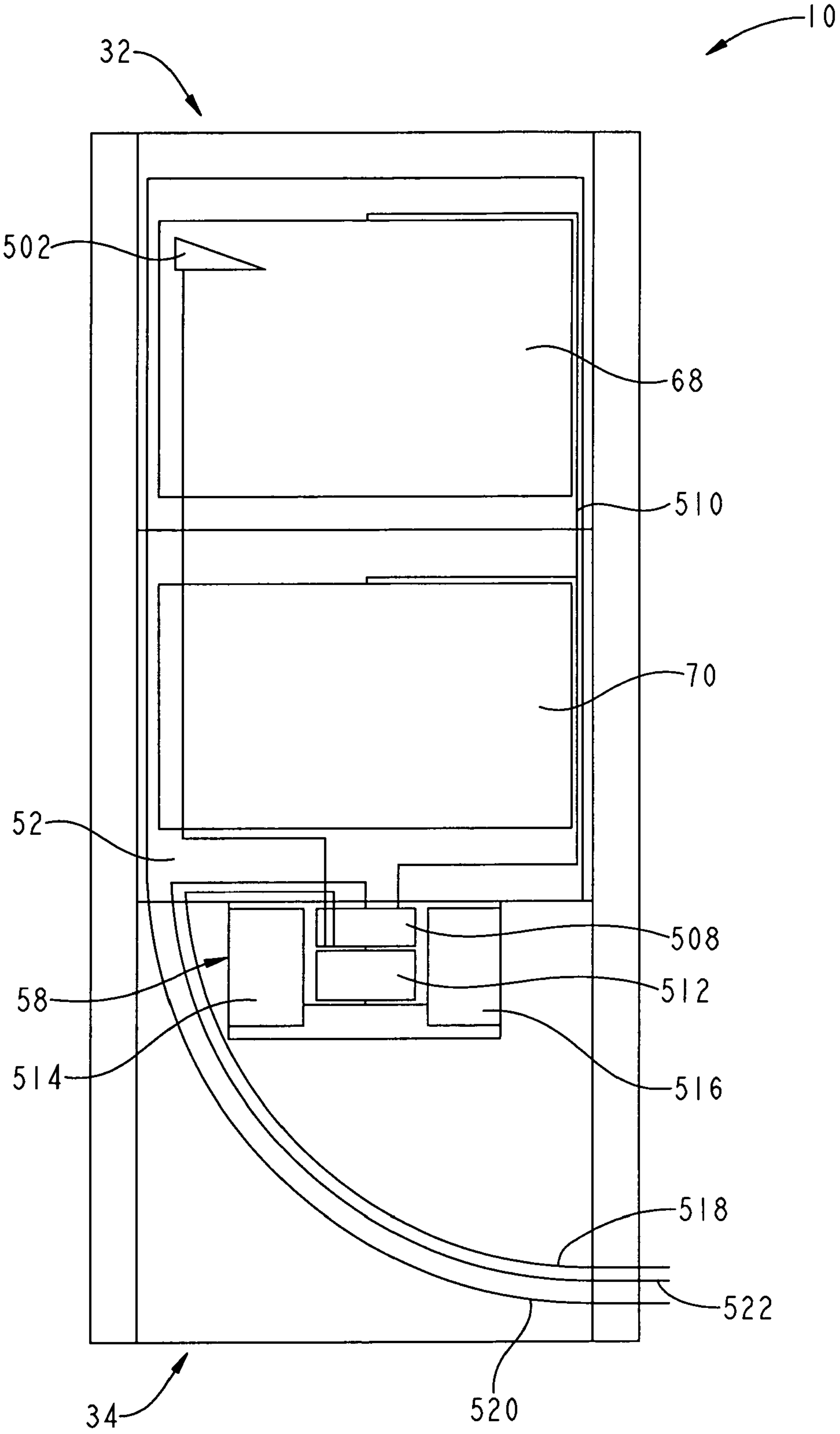
FIG. 4A and 4B are a simplified schematic diagram of the control system and the mattress assembly of the present invention.
Figure 4B:
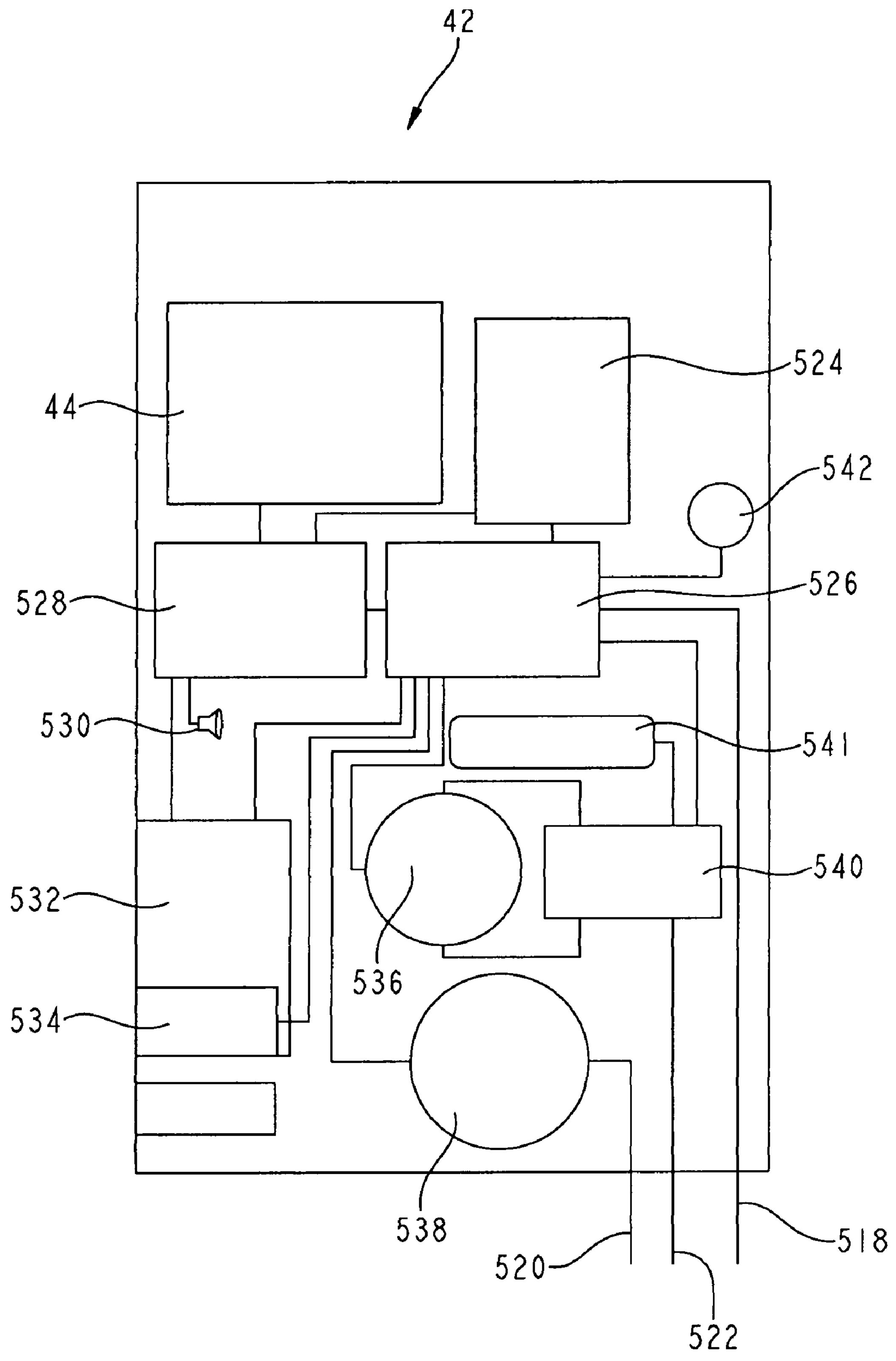

FIGS. 4A and 4B are a simplified schematic diagram of a control system and the patient support or mattress 10 of the present invention. FIG. 4A illustrates the patient support 10 including the various components of patient support 10 whereas FIG. 4B illustrates the control unit 42 and the various components. The patient support 10 includes the sensor pad 52 which is coupled to the pneumatic valve control box 58 as previously described. The sensor pad 52 includes a head sensor pad 68 and a seat sensor pad 70. The head sensor pad 68 is located at the head end 32 of the mattress 10. The seat sensor pad 70 is located at a middle portion of the mattress 10 which is located between the head end 32 and a location of the pneumatic valve control box 58. The seat sensor pad 70 is located such that a patient laying upon the mattress 10 may have its middle portion or seat portion located thereon when in a reclined state. In addition, when the head end 32 of the mattress 10 is elevated, the seat portion of the patient is located upon the seat sensor pad 70. As previously described with respect to FIG. 3, the head sensor pad 68 is located beneath the head section bladder assembly 60 and the seat sensor pad 70 is located beneath the seat section bladder assembly 62. Each one of the sensors of the head sensor pad 68 or the seat sensor pad 70 is located beneath one of the upstanding cylindrical bladders or cushions. A head angle sensor 502 is coupled to the control box 58 where signals received from the sensor 52 may provide head angle information and pressure adjustment information for pressure in the seat bladders 62.

The sensor pad 52 includes individual sensors, integrated electronics, and cabling to be described later herein in more detail. The sensor pad 52 is coupled through the associated cabling to the pneumatic control box 58. The pneumatic control box includes a multiplexer 508 coupled to the head sensor pad 68 and the seat sensor pad 70 through a signal and control line 510. The multiplexer board 508 is also coupled to an air control board 512 which is in turn coupled to a first valve block 514 and a second valve block 516. A communication/power line 518 is coupled to the control unit 42 of FIG. 4B. Likewise, a ventilation supply line 520 which provides for air flow through the patient support 10 for cooling as well as removing moisture from the patient is also coupled to the control unit 42 of FIG. 4B. An air pressure/vacuum supply line 522 is coupled to the control unit 42 as well.

The control unit 42 of FIG. 4B, also illustrated in FIG. 1, includes the display 44, which displays user interface screens, and a user interface input device 524 for inputting to the control unit 42 user selectable information, such as the selection of various functions or features of the present device. The selections made on the user interface input device 524 control the operation of the patient support 10, which can include selectable pressure control of various bladders within the mattress 10, control of the deck 6, for instance to put the bed 2 in a head elevated position, as well as displaying the current state of the mattress, deck position, and other features.

An algorithm control board 526 is coupled to the user interface input device 524. The algorithm control board 526 receives user generated input signals received through the input device 524 upon the selection of such functions by the user. The input device 524 can include a variety of input devices, such as pressure activated push buttons, a touch screen, as well as voice activated or other device selectable inputs. The algorithm control board 526 upon receipt of the various control signals through the user input device 524 controls not only the pressure regulation of the mattress 10 but also a variety of other devices which are incorporated into the control unit 42. For instance, the algorithm control board 526 is coupled to a display board 528 which sends signals to the display 44 to which it is coupled. The display board 528 is also connected to a speaker 530 which generates audible signals which might indicate the selection of various features at the input device 24. The algorithm control board 526 receives the required power from power supply 532 which includes an AC input module 534, typically coupled to a wall outlet within a hospital room.

The algorithm control board 526 is coupled to a compressor 536 and a blower 538. Both the compressor 536 and the blower 538 receive control signals generated by the algorithm control board 526. The compressor 536 is used to inflate the air bladders. The blower 538 is used for air circulation which is provided through the ventilation supply line 520 to the mattress 10. It is, however, possible that the compressor 536 may be used to both inflate the bladders and to circulate the air within the mattress 10. A pressure/vacuum switch valve 540 is coupled to the compressor 536 which is switched to provide for the application of air pressure or a vacuum to the mattress 10. A muffler 541 is coupled to the valve 540. In the pressure position, air pressure is applied to the mattress 10 to inflate the mattress for support of the patient. In the vacuum position, the valve 540 is used to apply a vacuum to the bladders therein such that the mattress may be placed in a collapsed state for moving to another location or to deflate bladders during turn assist. A CPR button 542 is coupled to the algorithm control board 526.

As illustrated, the algorithm control board 526, the compressor 536, the blower 538, and the user input device or user control module 524 are located externally to the mattress and are a part of the control unit 42 located on the footboard 38. The sensors and sensor pad 52, the pneumatic valve control box 58, and the air control board or microprocessor 512 for controlling the valves and the sensor pad system 52 are located within the mattress 10. It is within the present scope of the invention to locate some of these devices within different sections of the overall system, for instance, such that the algorithm control board 526 could be located within the mattress 10 or the air control board 512 could be located within the control unit 42.

Figure 5:
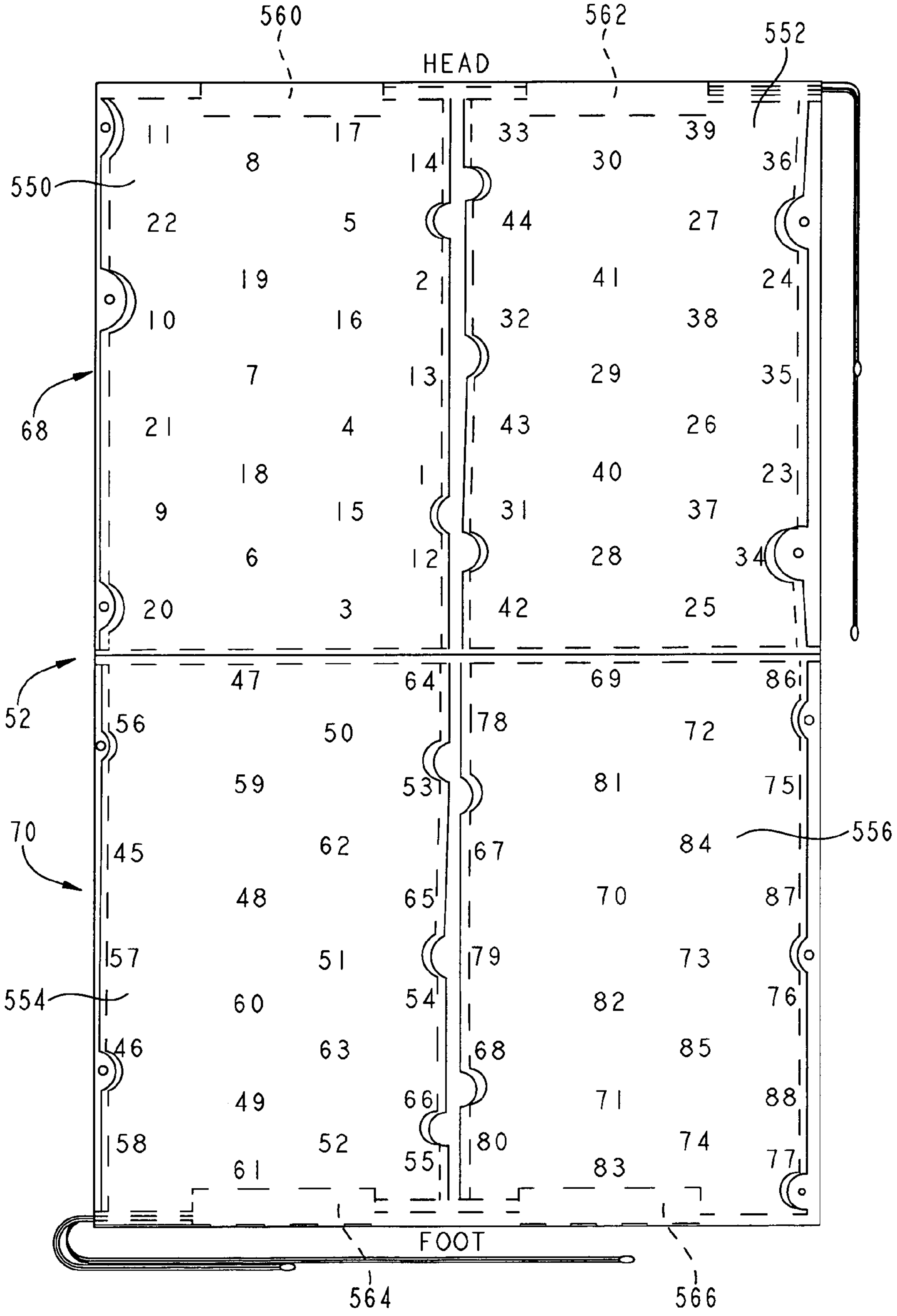
FIG. 5 illustrates a first and second sensor pad including a sequence of reading data from the sensors of the sensor pad.

FIG. 5 illustrates the sensor pad 52 including the head sensor pad 68 and the seat sensor pad 70. Each of the pads includes a plurality of sensors configured to provide a reflected wave energy signal is described in PCT Publication WO 2004/00678A1 having a publication date of 22 Jan. 2004, the disclosure of which is incorporated by reference herein. The sensor pads include fiber pairs which introduce wave energy, typically light, into a compressible medium such as foam. The light introduced to the foam is scattered in a manner dependent on the force applied to the surface of the foam. The reflected or scattered light energy is detected and converted to an electrical signal indicative of the force applied to the sensor. Both the head sensor pad 68 and seat sensor pad 70 each include 44 individual sensors spaced throughout. The location of each of individual pressure sensing elements is indicated by a number 1 through 88. The sensor pad 68 and the sensor pad 70 each include and can be considered as a collection of 44 independent interface pressure sensors. The areas between sensors are generally not sensitive to pressure. The signals or data generated by the sensors indicate a pressure distribution, the data being essentially a map of the interface pressure between the bottom of the bladder assembly and the deck or frame.

The head sensor pad 68 includes a first sensor group 550 and a second sensor group 552. The first sensor group 550 is located in an upper left quadrant of the sensor pad 52 whereas the second sensor group 552 is in an upper right quadrant of the sensor pad 52. Each of the individual sensor groups 550 and 552 include 22 sensors, the location of which is indicated and identified by a number. For instance, the first sensor group 550 includes sensors 1 through 22 and the second sensor group 552 includes sensors 23 through 44. The numerical order of the individual sensors indicates the sequence in which the information from each of these sensors is accessed by the multiplexer board 508.

The seat sensor pad 70 includes a third sensor group 554 and a fourth sensor group 556 configured to be substantially the same as the first sensor group 550 and the second sensor group 552 as previously described. Each of the sensor groups includes 22 sensors which have numbers indicating the sequence in which the signal 5 information is accessed or derived therefrom.

Each of the sensor groups 550, 552, 554, and 556 include an optical system device 560, 562, 564, and 566 respectively. Each of these devices includes a cable for connection to the pneumatic valve control box 58. Since each of the first sensor group 550, 552, 554, and 556 are substantially identical in construction, the optical system device 560 will be described and its description will apply to the remaining optical system devices 562, 564 and 566.

The optical system device 560 is an opto-electronics interface board including software embedded on a micro controller integrated with an opto-board and the sensor pad itself. The embedded software of the microprocessor is typically referred to as "firmware". As described in PCT publication WO 2004/006768A1, each of the sensors includes fiber optic cable which is coupled to the opto-electric board. Two light emitting diodes supply light to each of the individual sensors and a single photo diode array reads the optical inputs of all 22 sensors within a sensor group. An erasable programmable read only memory and a serial interface driver for communication are included. The primary purpose of the optical system device is to acquire the information sensed by each of the individual sensors which result from the reflected light which has been passed through the fiber optic cable to the individual sensor. Algorithms within the embedded microprocessor are used to linearize the data sensed by the sensors. The sensor data and diagnostic data are made available to the multiplexer 508 through RS-232 ports. Data is transmitted though the network 578, which may be a controller area network (CAN) bus, to the algorithm control unit 526.

Figure 6:
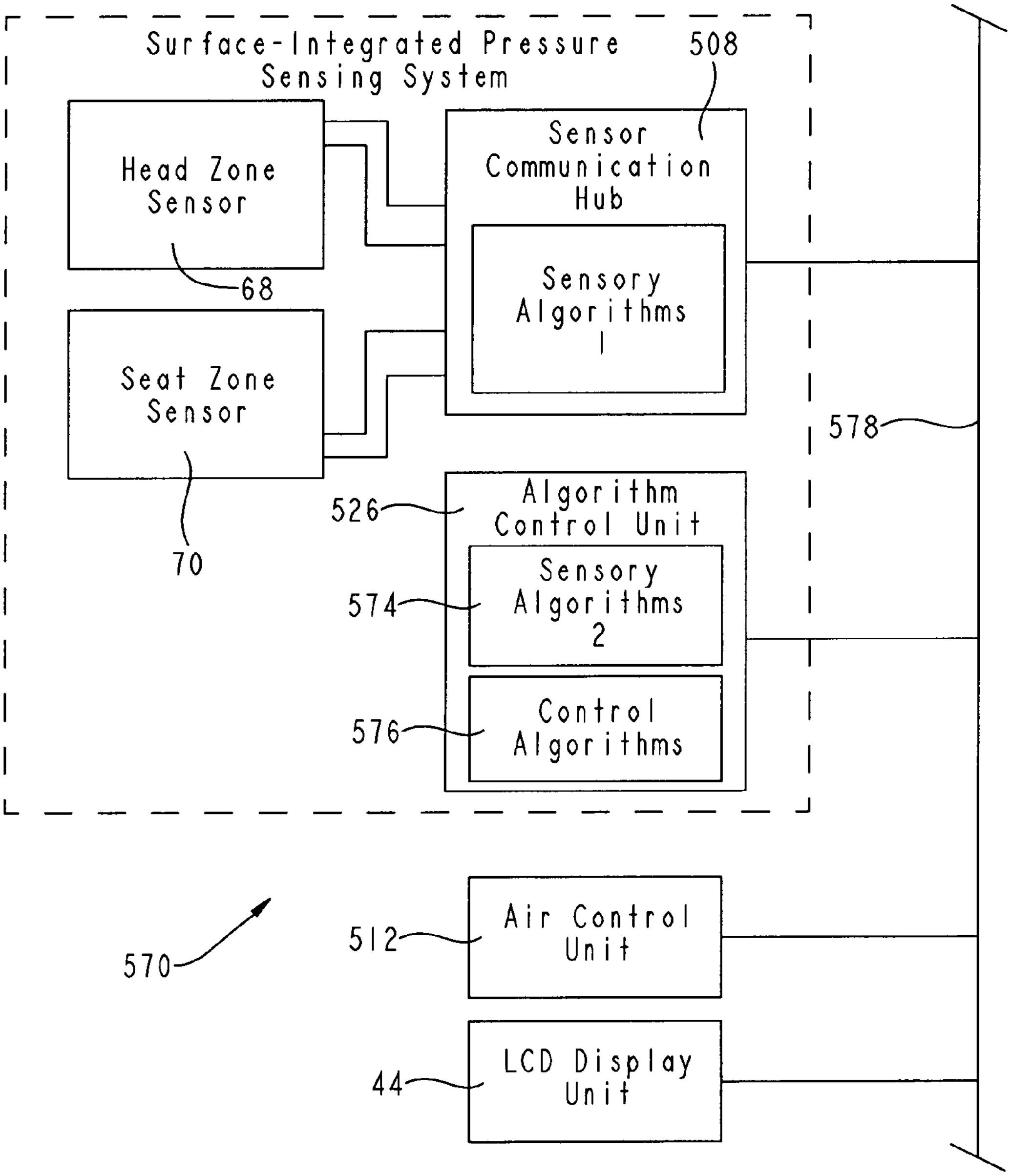
FIG. 6 illustrates a functional block diagram illustrating the head zone and seat zone sensors and other system components coupled to a communication network.

FIG. 6 illustrates an overall system architecture 570 of the present invention. As previously described, the multiplexer board 508, also known as a sensor communication hub, is coupled to the head zone sensor 68 and the seat zone sensor 70. The multiplexer 508 as well as the optical system devices includes a number of sensory algorithms to be described later herein. Also included in the system architecture 570 is the algorithm control unit 526 which includes a second set of sensory algorithms 574 and control algorithms 576. The output of the multiplexer 508 and the algorithm control unit 526 are coupled to a network 578 which is also coupled to the air control unit 512 and the LCD display unit 44. The network 578 includes interface hardware, also known as a communication hub. The network 578 acts as the communication bus for the various hardware, software, and firmware control devices.

As previously described, the multiplexer 508 includes the sensory algorithms 572. The algorithm control unit 526 also includes sensory algorithms which may include algorithms for providing pressure relief, for providing a motion metric, for providing weight estimation, and for providing information to a LCD module which includes a calculation of statistics model.

Figure 7:
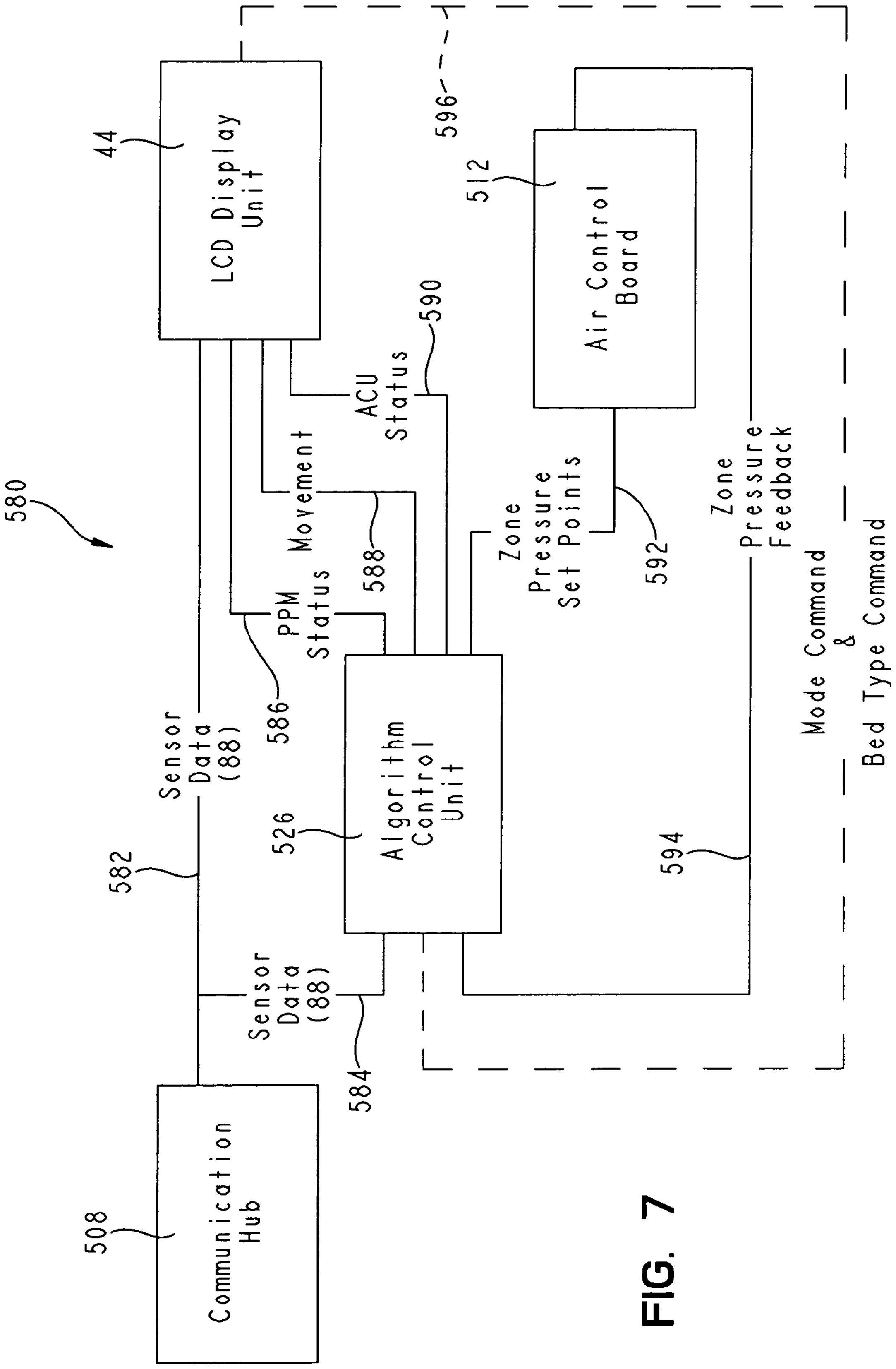
FIG. 7 illustrates a block diagram for a control system of the present invention including an algorithm control unit.

FIG. 7 illustrates a block diagram of a control system 580 incorporating the LCD display unit 44, the air control board 512, the communication hub or network 508, and the algorithm control unit 526. The communication hub 508 which receives sensor data from the head zone sensor 68 and the seat zone sensor 70 is coupled to both the LCD display unit 44 and the algorithm control unit 526 through a first sensor data line 582 and a second sensor data line 584 respectively. As described with respect to FIG. 6, the algorithm control unit 526 includes sensory algorithms 574 and control algorithms 576. The algorithm control unit 526 includes a first output line 586 coupled to the LCD display unit 44 for transmitting patient position monitor status, a second control line 588 for communicating movement status, and a third control line 590 for communicating the status of the algorithm control unit. In addition, the algorithm control unit 526 includes a fourth output line 592 which transmits the zone pressure set points for each of the head, seat and foot zones to the air control board 512 to which the line 592 is coupled. The air control board 512, which includes the pressure sensors previously described, sends control pressure zone feedback signals through a line 594 back to the algorithm control unit 526. The LCD display unit 44 through the user input interface device 524 also sends control signals to the algorithm control unit 526 through a control line 596 which includes signals such as various mode command signals as well as bed type command signals for adjusting the frame or deck of the bed.

As previously described in FIG. 6, the present invention includes sensory algorithms as well as control algorithms. The sensory algorithms are provided in firmware located within the multiplexer 508 and the algorithm control unit 526. Sensory algorithms include the following: bottom out detection, where a portion of the subject is supported by the bed frame as opposed to the surface, bed exit detection, sitting on the side of a bed detection, detection of a patient lying on the edge of the surface, detecting a lack of patient movement on the surface over a period of time, providing patient position monitoring by distinguishing between the following six positions left lying, left sitting, center lying, center sitting, right lying, right sitting, and measuring patient weight within plus or minus 20% within the bed and the flat position. The control system algorithms which are located in the control system algorithm firmware 576 optimize pressure reduction by dynamic load distribution adjustment of the surface air bladders of the mattress 10 located above the head sensor pad 68 and the seats sensor pad 70.

Figure 8:
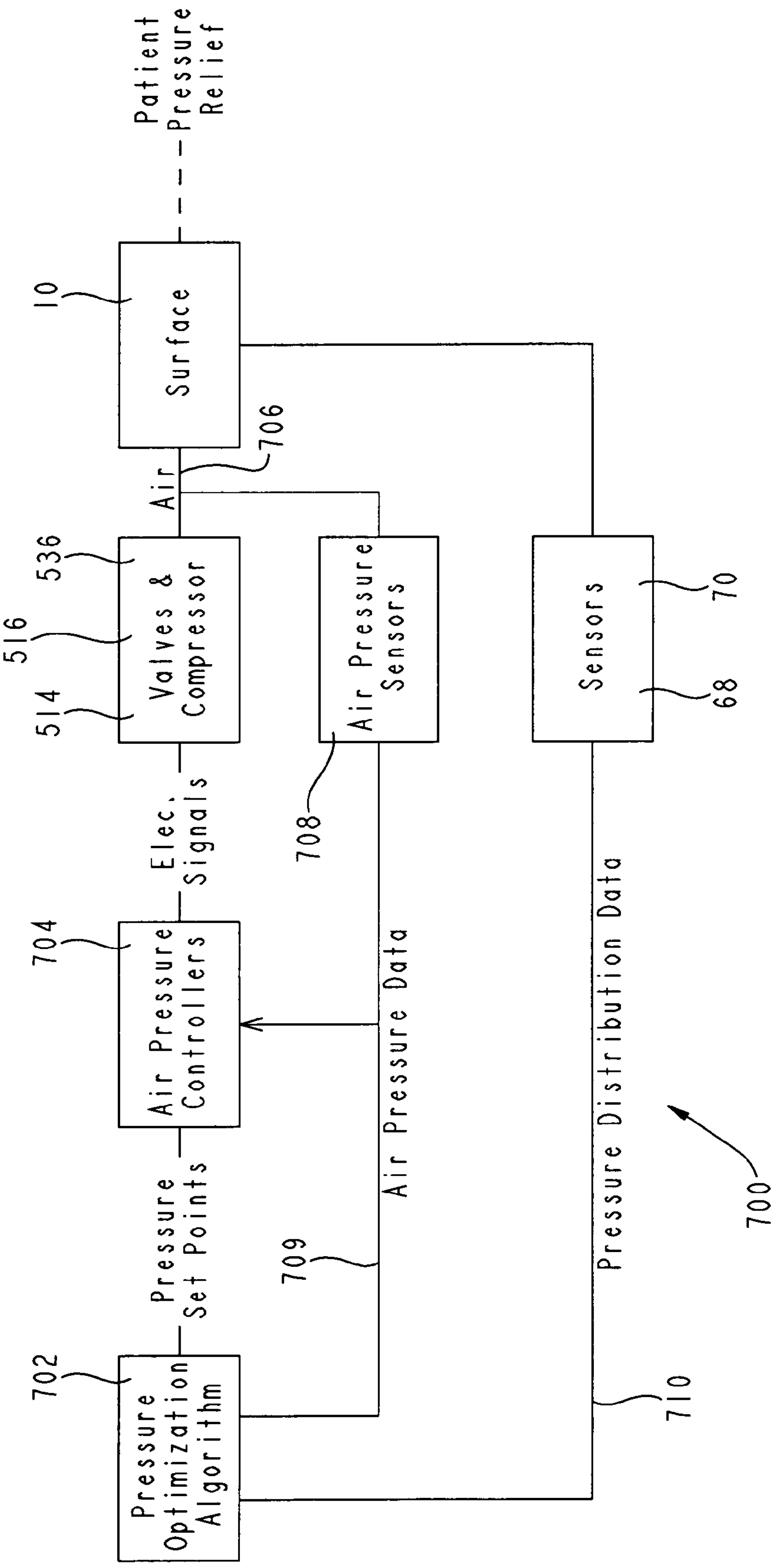
FIG. 8 illustrates a block diagram for a pressure optimization control system of the present invention.

FIG. 8 illustrates a block diagram for a pressure optimization control system 780 of the present invention. The control system provides closed loop feedback to find a preferred air pressure for supporting a patient. The air pressure located within the bladders located above the head sensor pad 68 and the seat sensor pad 70 is adjusted according to pressures sensed by pads 68 and 70. The patient to mattress interface pressure is not measured directly. Instead, the sensors located within the head sensor pad 68 and the seat sensor pad 70 sense the force or pressure transmitted through the associated head and seat bladder sections. The air pressure within each of these sections is measured by a pressure transducer located within the pneumatic valve control box 58.

As illustrated in FIG. 8, a pressure optimization algorithm 702, located within the control algorithm firmware section 576, transmits pressure set points stored or generated by the algorithm 702 to air pressure controllers located within the air control board 512. The air pressure controllers 704 generate control signals which are transmitted and coupled to the valves located within the first valve block 514, the second valve block 516, and to the compressor 536 located within the control unit 42. The controlled flow of air is provided to the surface 10 for pressure relief of the patient. The air within the air line 706 is coupled to and monitored by air pressure sensors 708 which transmit pressure signals through a line 709 to both the air pressure controller 704 and to the pressure optimization algorithm 702. In addition, the head sensor pad 68 and seat sensor pad 70 also measure the force supplied through the surface 10 and force sensing information is transmitted back to the pressure optimization algorithm 702 along a line 710.

Figure 9:
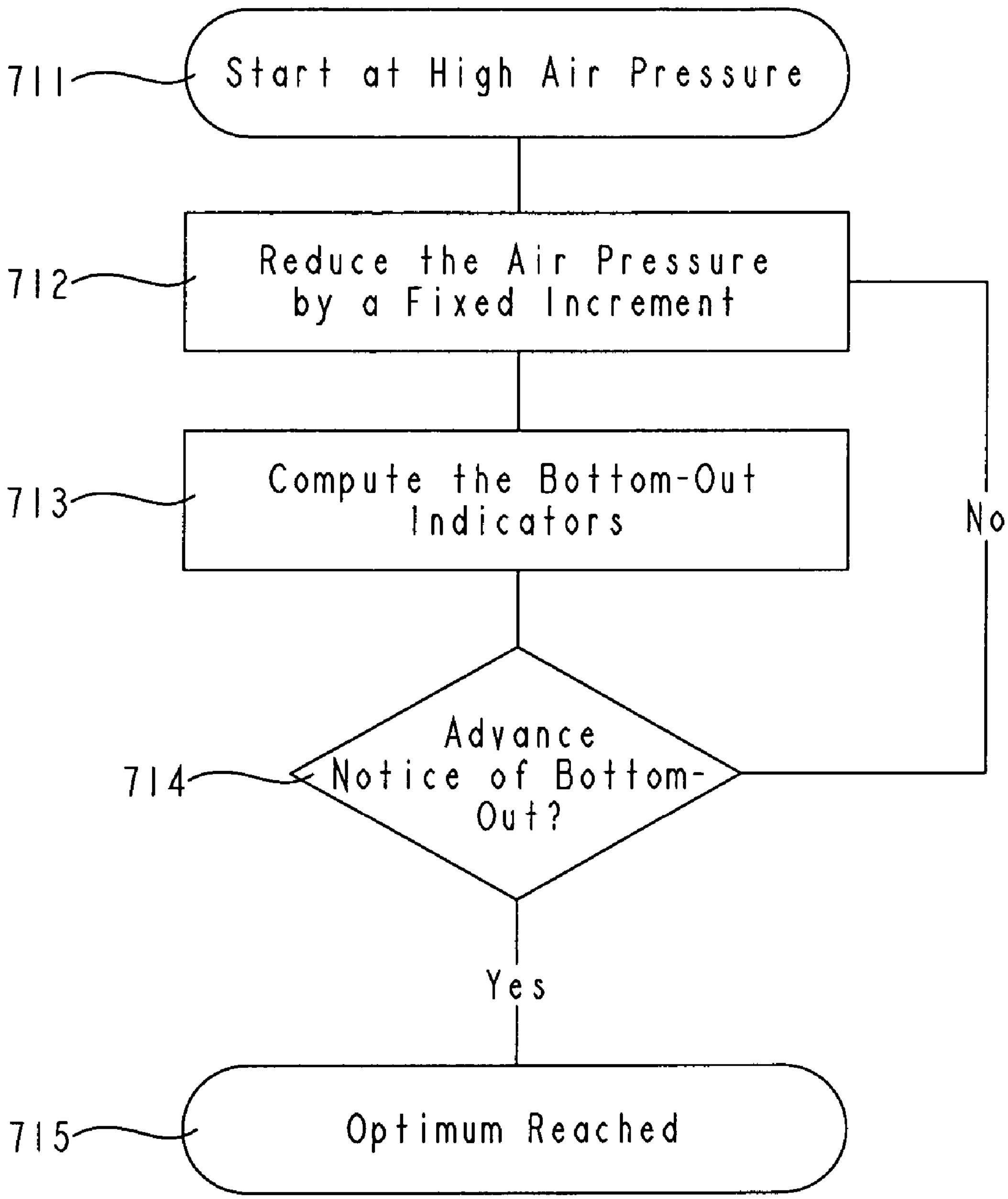
FIG. 9 illustrates a flow chart illustrating a method of determining a pressure for the patient support of the present invention.

FIG. 9 is a flowchart illustrating a method of determining a preferred pressure for the patient support of the present invention. The present invention provides for pressure relief within the air bladders by monitoring the air pressure within the bladders and controlling that air pressure through the detection of the force or pressure transmitted through the air bladders to the sensors located therebeneath.

Based on the assumption that the optimum air pressure is the pressure just prior to bottoming-out, this indication may be used as advance notification or as a signal that the optimum pressure has been reached. As shown in FIG. 9, the air pressure is reduced in increments. After each increment, the bottoming-out indicators are computed. At such time as the indicators provide notice of the bottoming-out trend, the air pressure is maintained at that setting, and the optimum pressure relief has been achieved. In principle, this algorithm may be used to automatically determine the optimum air pressure for different individuals and for different postures on the bed.

When the system is first turned on, the controller adjusts the air bladder pressures to a high air pressure at block 711. Initially, the bladders may be filled to 25 inches of water. The patient is then placed on the mattress where the mass of the patient is calculated according to a mass or weight algorithm. Once the mass of the patient has been calculated, the pressure within the bladders is lowered by fixed increments at block 712 of FIG. 9. As the pressure is lowered, the sensors of the sensor pads 68 and 70 are accessed according to the sequences previously shown in FIG. 5. The data or information provided by 22 of the sensors within each of the sensor groups is read or provided approximately every one quarter of a second. Consequently, the information from all of the first, second, third, and fourth sensor groups 550, 552, 554, and 556 are provided approximately every one second. This information is used to compute bottom-out indicators at block 714. The bottom-out indicators are derived from the pressure distribution data derived from the sensors from each of the sensor pads 68 and 70.

The bottom-out indicators are used to determine a bottoming-out trend. Such indicators may include:

(a) The sum of outputs of sensors over a "high pressure threshold." For this indicator, a threshold is set, and the amount by which the sensors exceed this threshold is accumulated. The high-pressure threshold may be fixed, or preferably, it may be computed from time to time in proportion to the average sensor output. It has been found that it is preferable to set the high-pressure threshold in the range of 1.2 to 3.0 times the average of all sensor outputs.

(b) The area not providing support, as measured by the number of sensors below a "support threshold". The "area not providing support" decreases when the support area increases. The support threshold may be fixed, or preferably, the support threshold may be computed from time to time in proportion to the average sensor output. It has been found that it is preferable to set the high-pressure threshold in the range of 0.1 to 0.7 times the average of all sensor outputs.

(c) The number of sensors over a high-pressure threshold. Similar to the indicator described in (a) above, a high-pressure threshold is set, and the number of sensors that exceed that high-pressure threshold is counted.

(d) The maximum output reported by any given sensor.

(e) The average value of the three sensors reporting the highest outputs.

(f) The standard deviation of all of the sensor outputs. This is calculated in accordance with the formula: standard deviation equals the square root of the sum of squared differences between the sensor output and the mean sensor output, divided by the number sensors minus one.

(g) The high-side deviation of sensor outputs. This indicator calculated in a similar manner to the standard deviation. In this case, however, only those sensor outputs that exceed the mean sensor output are used in the computation.

(h) The changes in the above indicators as a ratio to the change in bladder air pressure.

The pressure optimization algorithm 702 determines a distributed standard deviation of the data to provide an indicator which corresponds to a pressure within each of the head and seat bladder sections. As the distributed standard deviation trends toward a certain value, the air pressure is reduced continually at block 712 as long as the advance notice of bottoming-out at decision made at block 726 is not indicated. If, however, the advance notice of bottoming-out does occur as determined at decision block 714, then the preferred or optimum value of pressure is reached at block 715. The pressure optimization algorithm 702 then sends a signal to the air pressure controller 704 to maintain the pressure within the head and seat zones. The pressure or force transmitted through the head and seat zone bladders is continuously monitored and used to adjust the pressure within the bladders.

While the algorithm 702 reduces the air pressure by fixed increments at block 712 of FIG. 9, the firmware includes a reference table of patient weights and corresponding pressures. Initially, the bladder pressure of 25 inches of water is not incrementally dropped to a lower level. Instead, it is dropped by a larger amount, for instance 8 inches of water, to thereby reduce the time it takes for the system to reach the patient's optimized pressure profile. Since the table includes pressures correlated to patient weight, the system achieves an optimum state more quickly than if the pressure was reduced by fixed increments from the initially set pressure of 25 inches of water.

Figure 10:
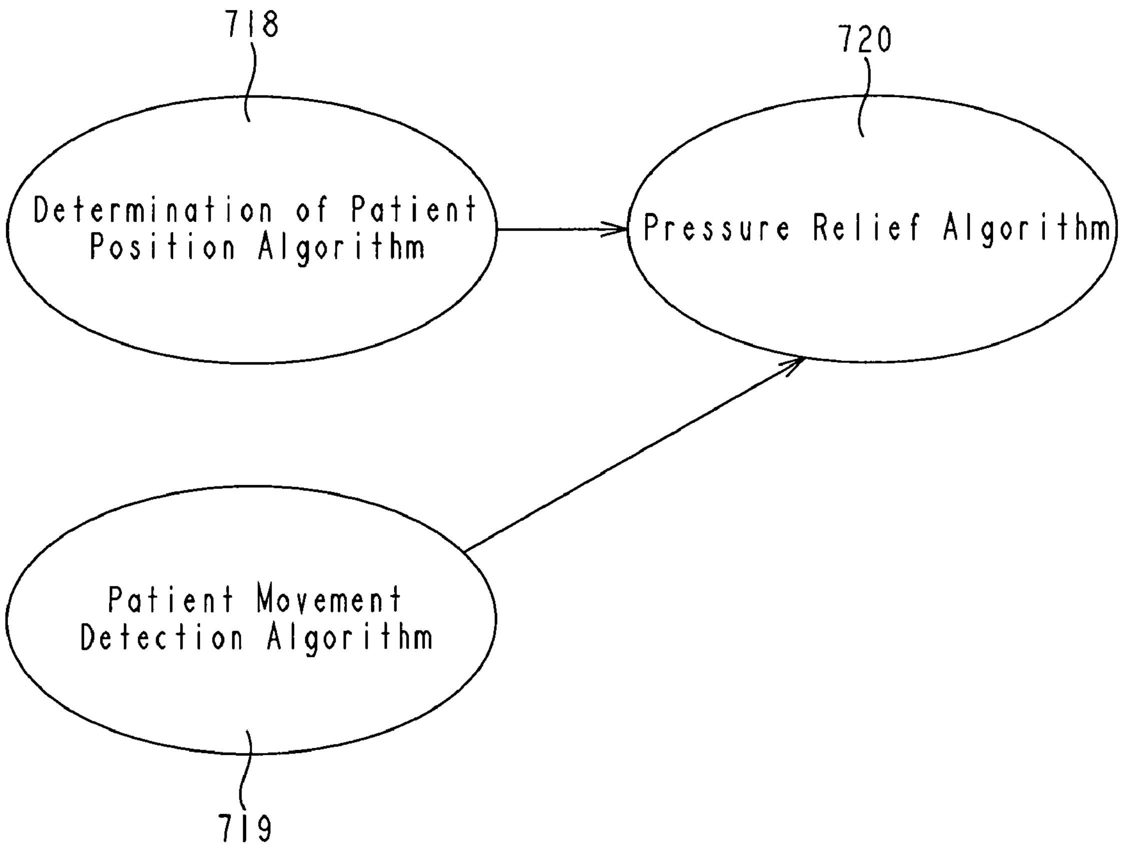
FIG. 10 illustrates a block diagram of algorithms of the present invention.

The flowchart with respect to FIG. 9, which determines a preferred pressure for the patient support of the present invention, may include a first algorithm 718 of FIG. 10 which determines the patient position and a second algorithm 719 which determines a patient movement or patient movement detection. The determination of patient position algorithm 718 determines the location of a patient by using the sensors 52 as previously described with respect to FIG. 5. Outputs from each of the individual sensors can be used to determine the location of the patient. The following patient locations or patient states are determined: Bed empty, centerline, left side lying, right side lying, left side sitting, right side sitting, and center sitting. In addition to the determination of the patient position, the patient movement detection algorithm 719 quantifies the amount of movement of a patient on the surface. This movement is quantified by monitoring the pressure changes which occur with respect to the bladders but which is sensed with the sensors 52. The output of the patient position algorithm 718 and the output of the movement detection algorithm 719 are used by a pressure relief algorithm 720. As generally described with respect to FIG. 9, the pressure relief algorithm reduces air pressure by fixed increments where the bottom-out indicators are used to detect advance notice of bottoming-out.

Figure 11:
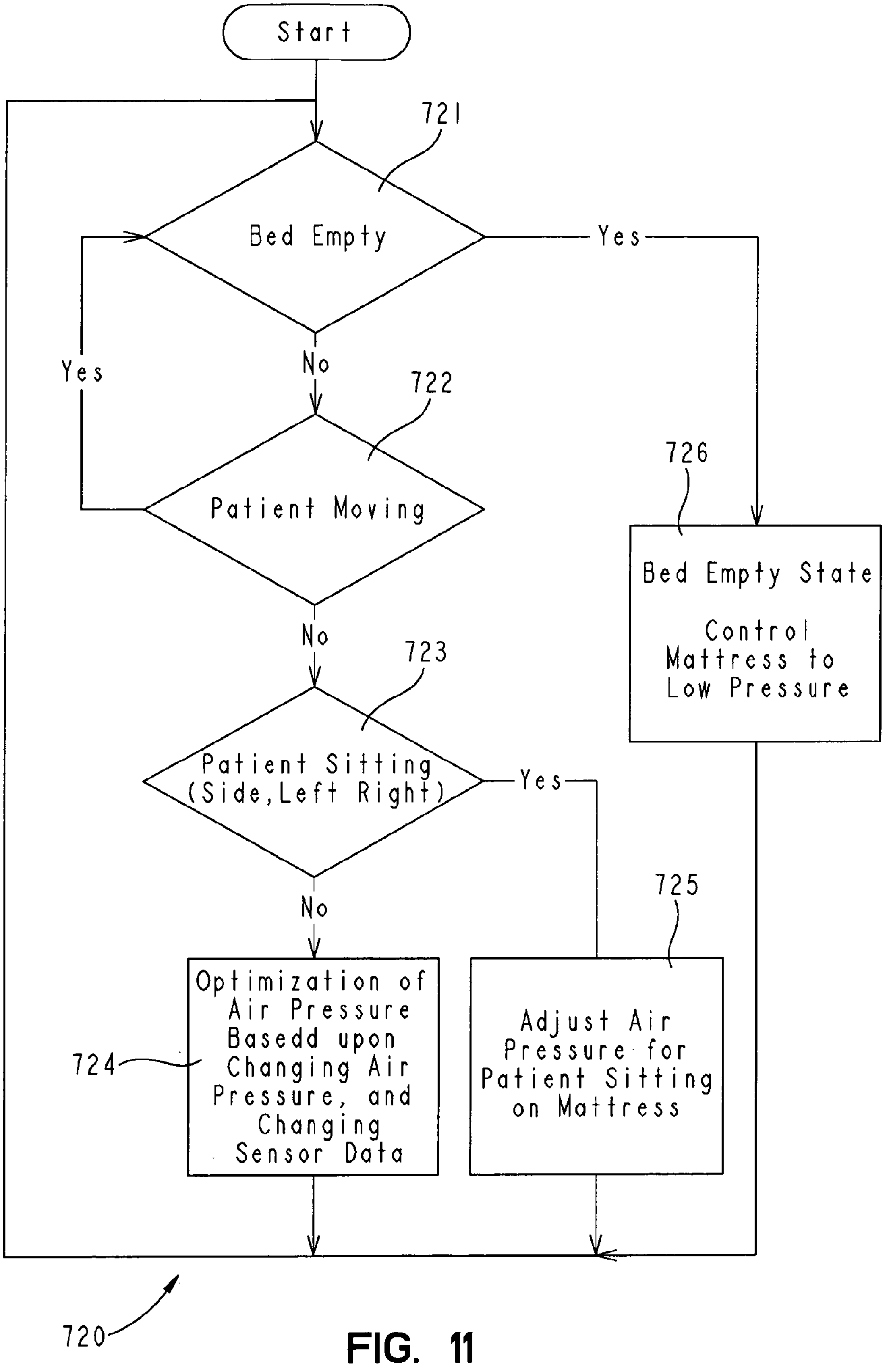
FIG. 11 illustrates a flowchart of optimizing pressure in the present invention.

FIG. 11 illustrates a flowchart of a method of optimizing air pressure for a patient. Initially the pressure relief algorithm 720 determines at a decision point 721 whether or not the bed is empty. If the bed is empty, the algorithm moves to a bed empty state 726 where the mattress pressure is set to a lower pressure since a patient is not located on the mattress. If, however, it is determined at step 721 that the bed is not empty, then the algorithm at step 722 determines whether or not the patient is moving. If the patient is moving, then the patient moving step 722 is repeated until it is determined that the patient is not moving. If the patient is not moving, the pressure relief algorithm 720 utilizes the patient position information which has been determined by the patient position algorithm 718. If the patient is sitting either on a left or right side at step 723 then the air pressure within the seat section is adjusted at step 725 for the patient sitting on the mattress. If, however, it is determined at step 723 that the patient is not in a sitting position the algorithm optimizes the air pressure. Air pressure is optimized and is based upon changing air pressures and changing sensor data to be described herein.

Figure 12:
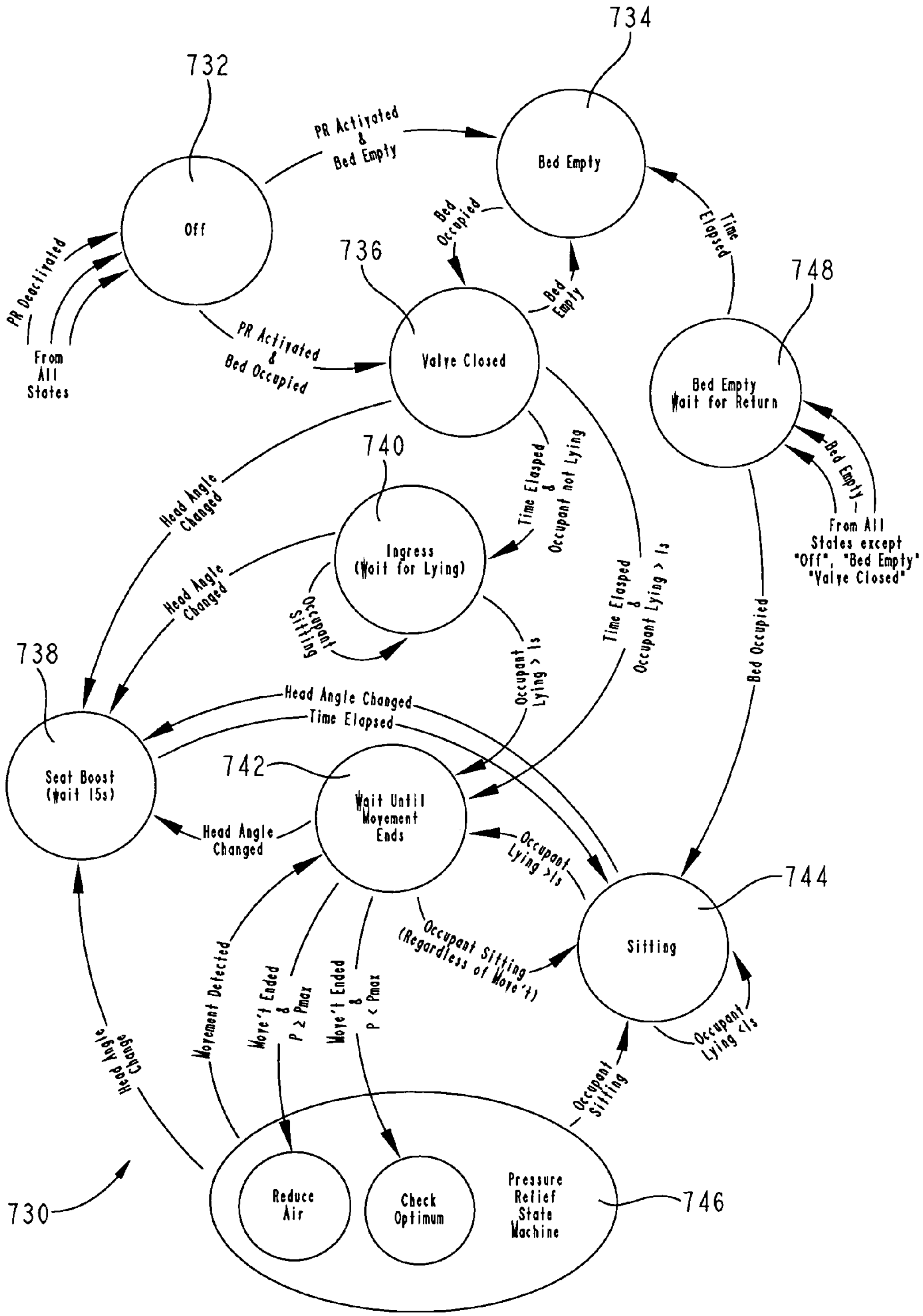
FIG. 12 illustrates a state machine diagram for a control system of the present invention.

FIG. 12 illustrates a state machine diagram for the control system of the present invention. The state machine diagram 730 indicates the various states of the present system which are enabled by firmware. The state machine represents the behavior of the present mattress system which is dependent upon the outcome of the various algorithms as well as the calculation of a number of indicators. The state machine diagram indicates the behavior of the system made in response to sensed conditions or derived values. These conditions and values include (1) indicators, (2) the patient position monitor, and (3) air pressure. In the figure, the curved arrows indicate the allowable transitions between states. The conditions that precipitate a transition from one state to another are labeled on each arrow.

Indicators are derived from the sensor outputs. For instance, the current state of each of these sensors is accessed over a period of time in the sequence previously described in FIG. 5. When that information is sensed over a period of time, the stored information may be used to develop an indicator. For instance, one of the indicators includes determining the standard deviation over the average. Indicators are calculated using the sensor outputs over a period of time and stored in memory. A change to the indicator may be compared to a predetermined threshold value or to other values which are based on the indicator values themselves. For instance, if the indicators are derived over a period of time, it is possible to determine the minimum indicator value during that period of time. The minimum indicator may then be used to calculate a threshold value equal to a percentage of that minimum value. That calculated value may then be compared to indicators to change from one state to another state.

In the present invention, the bottoming-out indicators, the standard deviation divided by the average over time, are used to provide advance notice of bottoming-out. An assumption is made that the optimum air pressure for an individual patient is at a pressure point just prior to bottoming-out. The indicators may then be used as an indication of the pressure within the bladder and whether it is increasing or decreasing. Consequently, bottoming-out can be predicted. Pressure is adjusted based on the predicted bottoming-out. Once the optimum pressure has been reached the pressure may be continually adjusted to maintain that pressure.

As previously described, after each increment or decrement of pressure, the bottoming-out indicators may be recomputed. Once the bottoming-out indicators provide advance notice of bottoming-out, then the air pressure is maintained at that setting and the optimum or preferred pressure relief is achieved. Such an algorithm provides a method to determine the optimum air pressure for a variety of individual patients and for different postures on the bed.

Referring now to FIG. 12, a state transition diagram for the patient support system is disclosed. Each one of the states represents a corresponding software function that may be embodied as software or firmware. Starting with an off state 732, the off state 732 may be entered from all of the states as well as when the pressure reduction (PR) is deactivated. (Pressure reduction may be deactivated by a user through the user interface 44.) A transition to a bed empty state 734 may be made by activating the pressure reduction as well as when the bed is empty. Once in the bed empty state 734, that state can be changed if it is determined that the bed is occupied. If it is determined that the bed is occupied while in the bed empty state 734, then the valve closed state 736 is entered. In addition, the valve closed state 736 may be entered from the off state when pressure reduction is activated and the bed is occupied.

In the valve closed state, the valves are closed for a set period of time while the system determines whether or not the occupant or patient or the frame itself transitions through a change of state. If while in the valve closed state 736, it is determined that the bed is empty, then the state transition diagram returns to the bed empty state at 734. If, however, if in the valve closed state 736, it is determined that the head angle has been changed, then the system moves to a seat boost state 738. In the seat boost state 738, the pressure in the seat is increased or boost for approximately 15 seconds. If, however, while in the valve closed state 736, the head angle is not changed but a certain period of time elapses and it is found that the occupant is not lying, then the system moves to the ingress state 740 which indicates that a patient is entering the bed. While in the ingress state 740 the system waits to determine whether or not the patient is in a lying position. If it is determined while in the ingress state 740 that the occupant is in a sitting position, then the state diagram maintains the ingress state 740.

Transition from the ingress state occurs if it is determined that the occupant or patient is lying for a period of greater than one second. The wait until the movement ends state 742 is entered. If while in the wait until the movement ends state 742, the head angle of the deck is changed, the system enters the seat boost state 738. If, however, it is determined that the occupant is sitting while in the state 742, the system moves to a sitting state 744. While the system determines that a patient is in a sitting position at state 744, as long as the patient or occupant is lying for less than one second, then the system remains in the sitting state 744. If while in the sitting state 744 the head angle is changed, the system moves to the seat boost state 738 in which the seat bladder is boosted for approximately 15 seconds. After that time has elapsed in the state 738, the system returns to the sitting state 744.

If while in the sitting state 744, it is determined that the occupant is lying for greater than one second, then the system transitions to the wait until the movement ends state 742. If the system determines that the movement has ended at state 742, then the system moves to the pressure relief state 746 under two conditions. Those two conditions are: 1) when the movement has ended and the pressure is greater than the maximum pressure or 2) when the movement has ended and the pressure is less than the force maximum. During the pressure relief state 746, pressure is adjusted for a patient in the prone position to be described in greater detail in FIG. 13. If the occupant, however, sits up during this state, then the system moves from the state 746 and returns to the sitting state 744. Likewise, if the head angle is changed while in the pressure relief state 746, then the system moves to seat boost state 738. The system can also leave the pressure relief state 746 when movement is detected. The detection of movement indicates that pressure relief is temporarily stopped until the movement ends at which point the system returns to the pressure relief state where the air pressure is continuously monitored and adjusted when necessary to provide optimum pressure relief. A bed empty wait for return state 748 may be entered when the patient leaves the bed. The bed empty wait for return state 748 may be entered from all states except the off state, the bed empty state 734, and the valve closed state 736.

Figure 13:
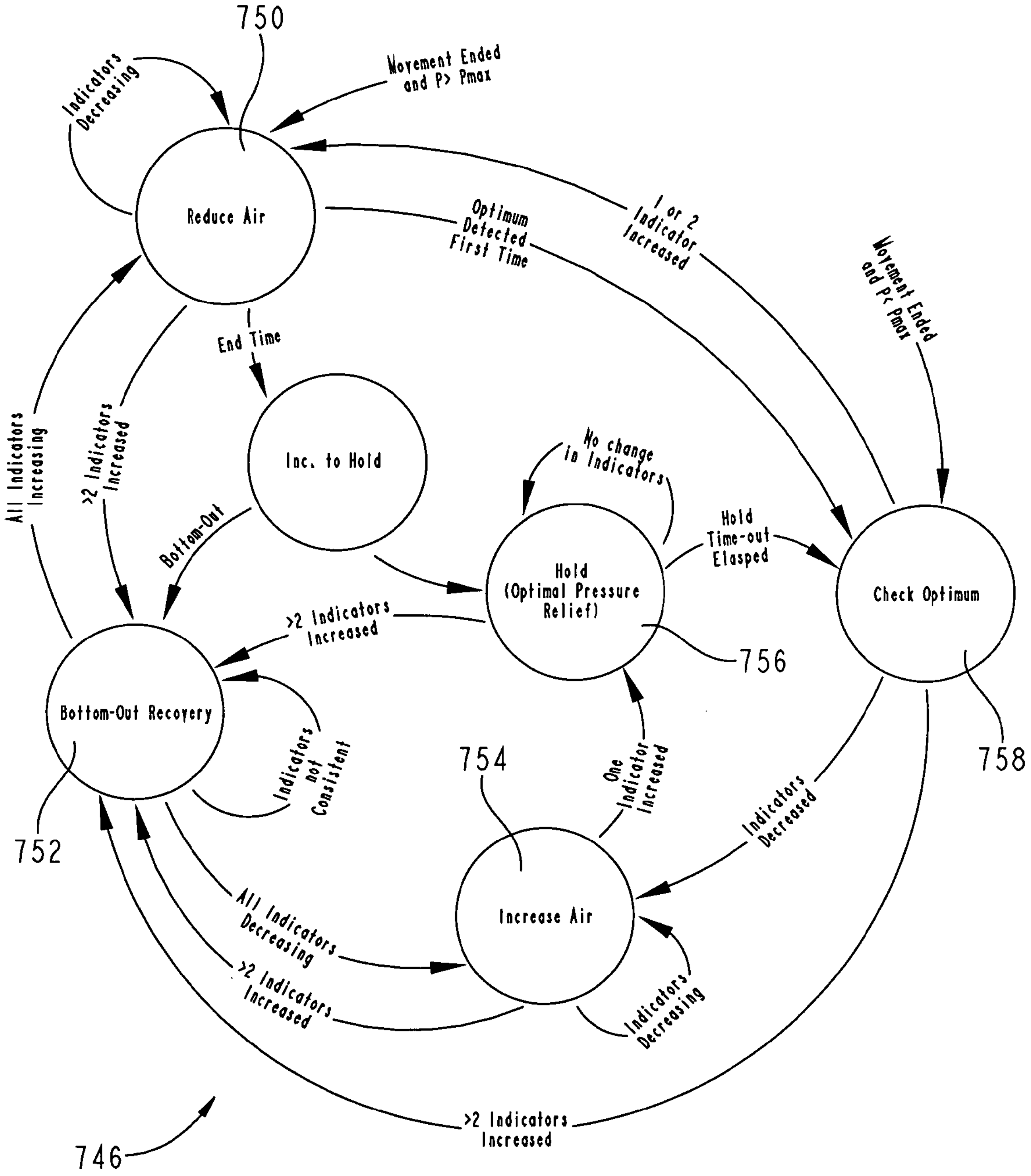
FIG. 13 illustrates a state machine diagram for a pressure relief control system of the present invention.

FIG. 13 illustrates a state transition diagram for the pressure relief state machine 746. As previously described, the bottoming-out indicators provide advance notice of bottoming-out. Based on the assumption that the optimum air pressure is the pressure just prior to bottoming-out, this advance notification is used as a signal that the optimum or preferred pressure has been reached. As previously described, air pressure is reduced in increments. After each increment the bottoming-out indicators may be computed. At the time that the bottoming-out indicators provide advance notice, then the air pressure maintained is that at that setting and the optimum or preferred pressure relief is achieved.

In the figure, the curved arrows indicate the allowable transitions between states. The conditions that precipitate a transition from one state to another are labeled on each arrow. In some cases, the reasons are based on a count of the number of indicators meeting a certain condition (eg. ">2 indicators decreasing"). It is to be understood that conditions may be replaced by comparing a single indicator (or weighted sum of indicators) against a suitable threshold.

If it is determined that the movement has ended and that P is greater than or equal to P max, then the air is reduced at a reduce air state 750. If it is determined that the indicators are decreasing, the system continues to reduce the air in the mattress bladders. If, however, it is determined that more than two indicators are increasing, the system enters a bottoming-out recovery state 752. The system remains in the bottoming-out recovery state if the indicators are not consistent. If, however, the indicators are increasing, then the system returns to the reduce air state 750. If, on the other hand, all indicators are decreasing, then the system enters an increase air state 754 where the air within the bladder is increased. The system remains in the increase air state 754 if all indicators are decreasing.

If more than two indicators increase, the system leaves the increase air state 754 and returns to the bottoming-out recovery state 752. If one indicator increases, then the system moves to the hold state 756 where the air pressure within the mattresses is maintained for the optimum or preferred pressure relief. If there are no changes to the indicators while in the hold state 756, the system remains in the optimal pressure mode. If, however, more than two indicators have increased while in the hold state 756, the system returns to the bottoming-out recovery state 752 as previously described. While in the hold state 756, a timer is set which enables the system to check for an optimum state at check optimum state 758 after the time out has elapsed. When in the check optimum state 758, if one or two indicators have increased, the system returns to the reduce air state 750 where the air in the bladders is reduced. If the optimum state is detected while in the reduced air state 750, the system moves to the check optimum state 758. A timer may also be set while in the reduce air state 750 whereupon at the end of the elapsed time the system returns to the hold pressure state 756. If during the transition 746 movement is detected the systems returns to the wait until movement ends stage 742 of FIG. 12.

When the bed is empty, the automatic control system is in the "Bed Empty" state. In this state, the control system sets the air pressure set-point to a value sufficient to fully inflate the air bladder.

It is known how to determine whether a patient has entered the bed (see for example, Lokhorst et al PCT international Publication WO 2004/006768) using an interface pressure sensor. Alternatively, other means, such as load cells in the legs of the bed frame or capacitive sensors or other types of bed occupant detection switches, may be employed to determine if a person occupies the bed. As soon as an occupant is detected, the automatic control system switches into the "valves closed" state. In this state, the automatic control system transmits instructions to the air pressure regulator to close off airflow in and out of the air bladder (essentially, to stop regulating the air pressure for the time being). When a fixed time period has elapsed, preferably about 5 to 30 seconds, the automatic control system switches into the "reduce air" state.

In the "reduce air" state, the automatic control system instructs the air regulator to reduce the air pressure by some increment. After a period of time, the indicators are computed. If the indicators have reduced, then the automatic control system remains in the "reduce air" state and initiates another decrement to the air pressure. If an indicator or two are found to have increased, then it means that the bottoming-out trend has started, and so the automatic control system switches to the "hold" state.

In the "hold" state, the automatic control system instructs the air regulator to maintain the air pressure at the value it was when the state was entered. Periodically, the indicators are computed. If there is no significant change in indicators, then the automatic control system remains in the "hold" state. If an indicator increases while in the "hold" state, it may be indicative of the occupant moving. In that case it is necessary to conduct a test to determine if the air pressure presently being maintained is optimal. This test is automatically conducted by switching to the "check optimum" state.

In the "check optimum" state, the automatic control system instructs the air pressure regulator to increment the air pressure by some interval. When the desired increase in air pressure has been achieved (or, alternatively, a reasonable length of time has elapsed), the indicators are computed. If the indicators decreased, it indicates that another increment in air pressure is required, so the system switches to the "increase air" state (which is subsequently described). As previously stated, the indicators were chosen so that minimum values are reached at or about the lowest air pressure prior to bottoming-out. Therefore, if the indicators decrease with increasing air pressure, then it indicates that the air pressure is still too low—further increasing the air pressure is likely to further reduce the indicators. If, on the other hand, the indicators generally increase after the increment in air pressure, then the opposite is true: the air pressure is now higher than optimum, and the system switches into the "reduce air" state.

In the "increase air" state, the automatic control system instructs the air regulator to increase the air pressure by some increment. After a period of time, the indicators are computed. If the indicators have reduced, then the automatic control system remains in the "increase air" state and initiates another increment to the air pressure. If an indicator or two are found to have increased, then it means that the bottoming-out trend has been reverted, and so the automatic control system switches to the "hold" state.

The foregoing description provides for the normal operation of the automatic control system. In practice, however, occasional events necessitate the addition of another state and several other state transitions. For example, the bed occupant may move while the system is in the "reduce air" state. This movement may cause one or more indicators to increase (where otherwise they would have continued to decrease), incorrectly causing the system to switch into the "hold" state. For this reason, it is preferable to set a limit on the length of time that the system remains in the "hold" state. When the time has elapsed, the system switches to "check optimum" state. It is preferable to make the time limit variable—the first instance that the "hold" state is entered since the bed is occupied, the time limit may be quite short, perhaps only a few seconds. When the system subsequently enters a "hold" state (after cycling through the "check optimum" and "reduce" air states), if the air pressure is similar to the last air pressure while in "hold" state, then the time limit may be set to a larger value, perhaps several minutes to hours in length.

Occasionally, the patient may move in a manner that causes the air bladder to bottom-out. For example, a patient who is initially lying down may sit up. Although the air pressure in the bladder was sufficient to support the occupant while lying, it is likely that it is not sufficient to support the occupant in a seated position, causing the air bladder to collapse and bottoming-out to occur. In general, when bottoming-out occurs, the indicators will steeply increase. The present system discriminates between the slight increase in indicators indicative of the bottoming-out trend starting to occur and the steep sudden increase in several indicators that is indicative of an actual bottom-out event. If, in any of the "reduce air", "hold", "check optimum", or "increase air" states, the more than two of the indicators increase, it indicates that a bottom-out event has occurred, and the automatic control system switches to "bottom-out recovery" state. In "bottom-out recovery" state, the automatic control system instructs the air regulator to increase the air pressure by some increment. After a period of time, the indicators are computed. If the indicators are not consistent with each other (i.e. some are increasing, others decreasing) it indicates that the system is still bottomed-out, and the automatic control system remains in "bottom-out recovery" state, and increments the air pressure set-point once again. If all the indicators are increasing, it indicates that the system has recovered from bottoming-out, and furthermore, the bottoming-out trend has reverted, and the automatic control system switches to "reduce air" state. If all of the indicators are decreasing, it indicates that the system has recovered from bottoming-out, but that the bottoming-out trend has not yet been reverted, and the automatic control system switches to "increase air" state.

The present invention includes features to control the stability of the control system by limiting the possible state transitions. For example, only one direct transition is permitted between "Reduce Air" to "Increase Air" states in order to avoid unstable behaviour (as evidenced by the system oscillating between those states). The permitted transition occurs only if maximum pressure is detected.

While this invention has been described with specific embodiments thereof, alternatives, modifications and variations may be apparent to those skilled in the art. Accordingly, it is intended to embrace all such alternatives, modifications and variations that fall within the spirit and broad scope of this appended claims.

The invention claimed is:

1. A pressure adjustable mattress system, comprising: a plurality of air bladders; a plurality of force sensors, each of the plurality of force sensors subtending at least one of the plurality of air bladders to sense a force transmitted through the subtended air bladder; a network, a control unit operably coupled to the network, a plurality of outputs, to transmit a signal representative of a sensed force to the network, each of the plurality of outputs coupled to at least one of the plurality of force sensors, the control unit being configured to continuously monitor the outputs, determine whether a person is supported by the air bladders, determine a position of a person supported b the air bladders determine whether a person supported by the air bladders is moving, and adjust pressure in the air bladders according to the person's position and according to whether the person is moving.

2. The pressure adjustable mattress of claim 1, wherein the plurality of force sensors comprise a light responsive device disposed in a compressible medium.

3. The pressure adjustable mattress of claim 2, further comprising a converter operatively coupled to each of the plurality of outputs, the converter including a digitizer to digitize the signal representative of the sensed force, and a filter, to filter the signal representative of the sensed force.

4. A method for adjusting the pressure of the air bladders of claim 1, to a pressure value, the mattress system including a plurality of force sensors located underneath the air bladders, wherein each of the plurality of force sensors generates a force signal representative of a sensed force transmitted through the air bladders of the pressure adjustable mattress system to the sensor, comprising: detecting, by force sensors located underneath air bladders, sensed forces transmitted through the air bladders, generating force signals representative of the sensed forces transmitted through the air bladders, ordering the force signals in a predetermined order; calculating an indicator signal as a function of the ordered force signals; comparing the indicator signal to the predetermined value to generate a correction signal; and adjusting the pressure of the air bladders of the pressure adjustable mattress system based on the correction signal.

5. The method of claim 4, wherein the ordering step comprises ordering the force signals in a predetermined order by reading the force signals in a predetermined sequence.

6. The method of claim 5, wherein the calculating step comprises calculating an indicator signal as a function of the ordered force signals by detecting a bottoming-out trend.

7. The method of claim 6, wherein the calculating step comprises calculating the indicator signal as a function of a standard deviation of the generated force signals.

8. In a pressure adjustable support, including a bladder to support a patient and having a pressure therein, a sensor subtending the bladder to sense a force transmitted through the bladder and generating a signal responsive to the sensed force, a method comprising the steps of: continuously detecting movement of the patient on the bladder with the sensor; continuously detecting changes in position of the patient on the bladder with the sensor; and adjusting the pressure within the bladder responsive to the detected position and the detected movement of the patient.

9. The method of claim 8, further comprising the step of pressurizing the bladder to an initial pressure.

10. The method of claim 9, the step of adjusting the pressure including reducing the initial pressure to a predetermined pressure.

11. The method of claim 10, the step of adjusting the pressure including reducing the predetermined pressure to a pressure determined according to the detected position of the patient and the detected movement of the patient.

12. The method of claim 11, the step of detecting the position of the patient including detecting a right side lying position and a left side lying position.

13. The method of claim 8, the step of detecting the movement of the patient step including detecting the patient in a sitting position.

14. The method of claim 13, the step of adjusting the pressure including adjusting the pressure within the bladder to a pressure sufficient for a patient in a sitting position.

15. In a pressure adjustable support, including a bladder assembly having a plurality of bladders, to support a patient, a plurality of sensors, each of the plurality of sensors subtending at least one of the bladders to sense a force transmitted through the bladders, a method comprising the steps of: detecting a first position of the patient on the plurality of bladders with the plurality of sensors; continuously detecting a quantity of movement of the patient on the plurality of bladders with the plurality of sensors; determining whether the patient is moving from the first position to a second position based on the quantity of movement; adjusting the pressure within the bladder responsive to the first position if the patient is determined to be not moving, and stopping adjustment of pressure within the bladder if the patient is determined to be moving from the first position to the second position.

16. The method of claim 15, further comprising the step of generating a plurality of signals responsive to the sensed force, each of the plurality of signals generated by one of the plurality of sensors.

17. The method of claim 16, further comprising reading each of the plurality of signals generated by each of the plurality of sensors in a predetermined order.

18. The method of claim 17, further comprising applying a mathematical function to the plurality of signals to determine an indicator signal to indicate a bladder pressure.

19. The method of claim 18, the step of reading each of the plurality of signals includes reading each of the plurality of signals over a predetermined time period.

20. The method of claim 19, the step of applying a mathematical function to each of the plurality of signals includes determining the standard deviation divided by the average.

* * * * *